(12) United States Patent
Dubreuil et al.

(10) Patent No.: US 12,083,507 B2
(45) Date of Patent: Sep. 10, 2024

(54) CATALYST COMPRISING AN ACTIVE NICKEL PHASE IN THE FORM OF SMALL PARTICLES DISTRIBUTED IN A SHELL AND A NICKEL-COPPER ALLOY

(71) Applicant: IFP Energies nouvelles, Rueil-Malmaison (FR)

(72) Inventors: Anne-Claire Dubreuil, Rueil-Malmaison (FR); Malika Boualleg, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 353 days.

(21) Appl. No.: 17/630,672

(22) PCT Filed: Jul. 16, 2020

(86) PCT No.: PCT/EP2020/070078
§ 371 (c)(1),
(2) Date: Jan. 27, 2022

(87) PCT Pub. No.: WO2021/018600
PCT Pub. Date: Feb. 4, 2021

(65) Prior Publication Data
US 2022/0266225 A1  Aug. 25, 2022

(30) Foreign Application Priority Data

Jul. 31, 2019  (FR) ........................................ 1908724

(51) Int. Cl.
*B01J 23/755* (2006.01)
*B01J 21/04* (2006.01)
(Continued)

(52) U.S. Cl.
CPC ............. *B01J 23/755* (2013.01); *B01J 21/04* (2013.01); *B01J 23/72* (2013.01); *B01J 35/647* (2024.01);
(Continued)

(58) Field of Classification Search
CPC . B01J 23/755; B01J 21/04; B01J 23/72; B01J 35/647; B01J 37/0205;
(Continued)

(56) References Cited

U.S. PATENT DOCUMENTS 5,948,942 A    9/1999   Agudela et al.
8,586,808 B2  11/2013   Dubreuil et al.
(Continued)

FOREIGN PATENT DOCUMENTS

FR    2927267 A1    8/2009
FR    3064500 A1   10/2018
FR    3076746 A1    7/2019

OTHER PUBLICATIONS

International Search Report for PCT/EP2020/070078 dated Sep. 2, 2020.
(Continued)

*Primary Examiner* — Prem C Singh
*Assistant Examiner* — Francis C Campanell
(74) *Attorney, Agent, or Firm* — MILLEN, WHITE, ZELANO & BRANIGAN, P.C.; Csaba Henter

(57) ABSTRACT

Nickel and copper catalyst, and an alumina support:
  nickel distributed both in the core of and on a crust at the periphery of the support, crust thickness being 2% to 15% of catalyst diameter;
  nickel density ratio between the crust and the core greater than 3;
  crust contains more than 25% by weight of nickel element relative to total weight of nickel in the catalyst;
(Continued)

mole ratio between nickel and copper is 0.5 to 5,
at least one portion of nickel and copper is a nickel-copper alloy;
nickel content in the nickel-copper alloy is 0.5% to 15% by weight of nickel element relative to total weight of the catalyst;
size of the nickel particles in the catalyst is less than 7 nm.

18 Claims, 1 Drawing Sheet

(51) Int. Cl.
    *B01J 23/72*     (2006.01)
    *B01J 35/64*     (2024.01)
    *B01J 37/02*     (2006.01)
    *B01J 37/08*     (2006.01)
    *C10G 45/36*     (2006.01)

(52) U.S. Cl.
    CPC ....... *B01J 37/0205* (2013.01); *B01J 37/0236* (2013.01); *B01J 37/088* (2013.01); *C10G 45/36* (2013.01); *C10G 2300/1037* (2013.01); *C10G 2300/301* (2013.01); *C10G 2300/70* (2013.01)

(58) Field of Classification Search
    CPC ...... B01J 37/0236; B01J 37/088; B01J 35/19; B01J 35/397; B01J 35/613; B01J 23/002; B01J 35/635; B01J 37/0203; B01J 35/615; B01J 35/633; B01J 37/10; C10G 45/36; C10G 2300/1037; C10G 2300/301; C10G 2300/70; C10G 45/48; Y02P 20/52; C07C 2521/04; C07C 2523/72; C07C 2523/755; C07C 5/09; C07C 5/03; C07C 5/05
    USPC .................................. 585/270; 502/331, 335
See application file for complete search history.

(56) References Cited

U.S. PATENT DOCUMENTS

2010/0324346 A1     12/2010   Dubreuil et al.
2012/0065442 A1*   3/2012   Geyer .................... B01J 35/393
                                          977/773

OTHER PUBLICATIONS

Kang, M. et al., "γ-Alumina Supported Cu—Ni Bimetallic Catalysts: Characterization and Selective Hydrogenation of 1,3-Butadiene," The Canadian Journal of Chemical Engineering, Feb. 2002, vol. 80, pp. 63-70.
English Abstract for FR-3064500, Publication Date: Oct. 5, 2018.
English Abstract for FR-3076746, Publication Date: Jul. 19, 2019.

* cited by examiner

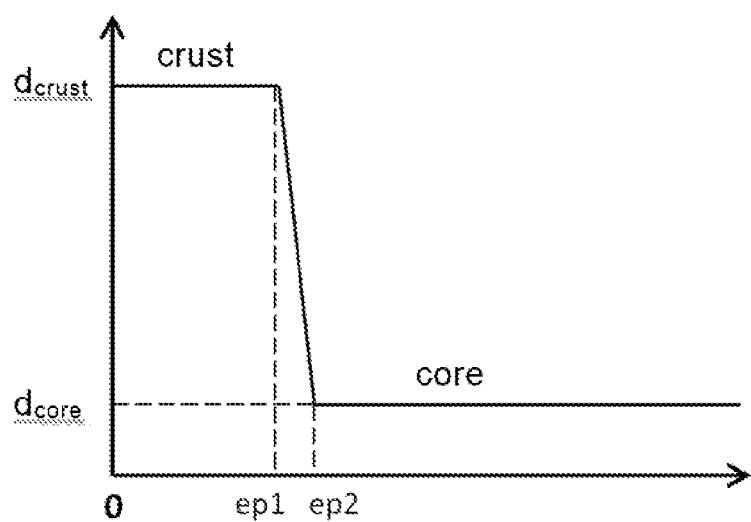

CATALYST COMPRISING AN ACTIVE NICKEL PHASE IN THE FORM OF SMALL PARTICLES DISTRIBUTED IN A SHELL AND A NICKEL-COPPER ALLOY

TECHNICAL FIELD

The present invention relates to a supported metal catalyst based on nickel and copper intended particularly for the hydrogenation of unsaturated hydrocarbons, and more particularly for the selective hydrogenation of polyunsaturated compounds or the hydrogenation of aromatics.

PRIOR ART

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ gasoline fraction (gasolines containing hydrocarbon compounds having 5 or more carbon atoms), in particular styrene or indene compounds. These polyunsaturated compounds are highly reactive and result in side reactions in the polymerization units. It is thus necessary to remove them before making economic use of these fractions.

Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes.

Selective hydrogenation catalysts are generally based on metals from Group VIII of the Periodic Table, preferably palladium or nickel. The metal is in the form of metal particles deposited on a support. The metal content, the size of the metal particles and the distribution of the active phase in the support are among the criteria which have an influence on the activity and the selectivity of the catalysts.

The macroscopic distribution of the metal particles in the support constitutes an important criterion, mainly in the context of rapid and consecutive reactions such as selective hydrogenations. It is generally desirable for these elements to be located in a crust at the periphery of the support in order to avoid problems of intragranular material transfer which may result in activity defects and a loss of selectivity. Such catalysts are also referred to as "eggshell" catalysts.

Such catalysts are widely known in the case of selective hydrogenation catalysts based on palladium. Indeed, owing to the low palladium content (generally less than 1% by weight (1 wt %) of palladium relative to the catalyst) and suitable preparation processes, a thin crust of palladium at the periphery of the support grains can be obtained (FR2922784, US2010/217052).

It is often proposed to replace palladium with nickel, a metal which is less active than palladium, and which it is therefore necessary to have in a larger amount in the catalyst. Thus, nickel-based catalysts generally have a metal content of between 5% and 50% by weight of nickel relative to the catalyst. In these catalysts, the nickel is generally distributed homogeneously within the support. One possible way of improving these catalysts in terms of activity and selectivity is to control the distribution of nickel within the support by depositing the nickel in a more concentrated manner on a crust, at the periphery of the support. Such catalysts are known from the prior art.

Document U.S. Pat. No. 4,519,951 describes an "eggshell" catalyst with nickel on a porous support having a pore volume of at least 0.2 ml/g for the pores having a size of less than 11.7 nm and a pore volume of at least 0.1 ml/g for the pores having a size of greater than 11.7 nm. More than 50% of the nickel is found in a crust, the thickness of which is equal to 0.15 times the radius of the support. This catalyst is used for the hydrogenation of fats.

Document CN101890351 describes a supported nickel catalyst in which more than 90% of the nickel is found in a 700 μm-thick crust. The catalyst is prepared using an ammoniacal solution to dissolve the nickel salt. These catalysts are used in a selective hydrogenation application.

Document US2012/0065442 describes a supported nickel catalyst in which the size distribution of the nickel crystallites is bimodal with 30% to 70% of the nickel crystallites having a mean size (diameter) of 1.0 to 2.5 nm, the remaining nickel crystallites having a mean size (diameter) of 3.0 to 4.5 nm. The nickel is distributed both on a crust with a thickness of 3% to 15% of the diameter and at the core, the nickel concentration ratio between the crust and the core being between 3.0:1 and 1.3:1. At least 75% of the pore volume is found in pores having a size of more than 5.0 nm.

OBJECTS OF THE INVENTION

Surprisingly, the applicant has discovered that by applying a specific hydrothermal treatment after the addition of a particular organic additive to a catalyst based on nickel and copper (and in which an alloy based on nickel and copper is formed on the support) comprising an alumina support obtained according to a very specific method, a catalyst is obtained in which at least a portion of the nickel is distributed over a crust at the periphery of the support, the other portion of the nickel being distributed in the core of the catalyst. Without wishing to be bound by any theory, the hydrothermal treatment carried out after the step of bringing a specific organic additive into contact with the catalyst based on nickel and copper on a particular alumina support, having undergone a hydrothermal treatment in the presence of an acid solution, seems to cause the nickel to migrate at least in part from the interior of the support to the periphery of the support, thus forming a nickel crust. Furthermore, it has been observed by the applicant that, during the preparation of the catalyst, carrying out a step of bringing the support into contact with a solution simultaneously containing a copper-based metal precursor and a nickel-based metal precursor, followed by a step of drying and reducing in the presence of a reducing gas at low temperature (between 150° C. and 250° C.) makes it possible to obtain a nickel-copper alloy (in reduced form) which unexpectedly makes it possible to greatly improve the reducibility of the nickel active phase on the support. Furthermore, the presence of copper in the catalyst makes it possible to maintain good activity and a longer service life of the catalyst when the latter is put in contact with a hydrocarbon feedstock comprising sulfur. Indeed, compared to nickel, the copper present in the catalyst more easily captures the sulfur-containing compounds included in the feedstock, which limits the irreversible poisoning of the active sites.

The present invention thus relates to a new type of catalyst which, by virtue of its specific preparation process, makes it possible to obtain a catalyst comprising performance qualities at least as good, or even better, in terms of activity and selectivity within the context of the selective hydrogenation reactions of polyunsaturated compounds or hydrogenation reactions of polyunsaturated aromatics, while using a lower amount of nickel phase than that typically used in the prior art, which is due to a better distribution of the nickel active phase in the support, making the latter more accessible to the reagents and also to a nickel particle size of less than 7 nm, imparting an even greater intrinsic activity of the nickel. The presence of an NiCu alloy also makes it possible to carry out a step of reducing the metal elements in the presence of a reducing gas at lower temperatures and shorter reaction times than those commonly used in the prior art. Advantageously, the use of less severe operating conditions than in the prior art makes it possible to directly carry out the reduction step within the reactor in which it is desired to carry out the selective hydrogenation of polyunsaturated fractions.

A first subject according to the invention relates to a catalyst comprising nickel and copper, in a proportion of 1% and 50% by weight of nickel element relative to the total weight of the catalyst, and a second metallic element of copper, in a proportion of 0.5% to 15% by weight of copper element relative to the total weight of the catalyst, and an alumina support, said catalyst being characterized in that:
- the nickel is distributed both on a crust at the periphery of the support, and in the core of the support, the thickness of said crust being between 2% and 15% of the diameter of the catalyst;
- the nickel density ratio between the crust and the core is strictly greater than 3;
- said crust comprises more than 25% by weight of nickel element relative to the total weight of nickel contained in the catalyst;
- the mole ratio between nickel and copper is between 0.5 and 5;
- at least one portion of the nickel and copper is in the form of a nickel-copper alloy;
- the nickel content in the nickel-copper alloy is between 0.5% and 15% by weight of nickel element relative to the total weight of the catalyst,
- the size of the nickel particles in the catalyst is less than 7 nm.

Advantageously, the nickel density ratio between the crust and the core is between 3.8 and 15.

Advantageously, said crust comprises more than 40% by weight of nickel element relative to the total weight of nickel contained in the catalyst.

Advantageously, the transition interval between the core and the crust of the catalyst is between 0.05% and 3% of the diameter of the catalyst.

Advantageously, the sulfur content of the alumina support is between 0.001% and 2% by weight relative to the total weight of the alumina support, and the sodium content of said alumina support is between 0.001% and 2% by weight relative to the total weight of said alumina gel.

Advantageously, the thickness of said crust is between 2.5% and 12% of the diameter of the catalyst.

Advantageously, the nickel density ratio between the crust and the core is greater than 3.5.

Another subject according to the invention relates to a process for preparing a catalyst according to the invention, said process being characterized in that:
a) an alumina gel is provided;
b) the alumina gel from step a) is shaped;
c) the shaped alumina gel obtained at the end of step b) is subjected to a heat treatment comprising at least one hydrothermal treatment step in an autoclave in the presence of an acid solution, at a temperature of between 100° C. and 800° C., and at least one calcining step, at a temperature of between 400° C. and 1500° C., carried out after the hydrothermal treatment step, in order to obtain an alumina support;
d) the sequence of the following sub-steps is carried out:
   d1) the alumina support is brought into contact with at least one nickel precursor in order to obtain a catalyst precursor,
   d2) the catalyst precursor obtained at the end of step d1) is dried at a temperature below 250° C.;
   d3) the dried catalyst precursor obtained at the end of step d2) is brought into contact with at least one solution containing at least one organic additive chosen from aldehydes containing 1 to 14 carbon atoms per molecule, ketones or polyketones containing 3 to 18 carbon atoms per molecule, ethers and esters containing 2 to 14 carbon atoms per molecule, alcohols or polyalcohols containing 1 to 14 carbon atoms per molecule and carboxylic acids or polycarboxylic acids containing 1 to 14 carbon atoms per molecule, the mole ratio between the organic additive and the nickel being greater than 0.05 mol/mol;
   d4) a hydrothermal treatment of the catalyst precursor obtained at the end of step d3) is carried out at a temperature between 100° C. and 200° C. for a period of between 30 minutes and 5 hours under a gas stream comprising between 5 and 650 grams of water per kg of dry gas;
e) the sequence of the following sub-steps is carried out:
   e1) the alumina support is brought into contact with at least one solution containing at least one copper precursor and one nickel precursor at a desired nickel concentration in order to obtain, on the final catalyst, a content of between 0.5% and 15% by weight of nickel element relative to the total weight of the final catalyst;
   e2) at least one step of drying the catalyst precursor obtained at the end of step e1) is carried out at a temperature below 250° C.;
steps d) and e) being carried out separately in any order,
f) the alumina support is brought into contact with at least one solution containing at least one organic compound comprising at least one carboxylic acid function, or at least one alcohol function, or at least one ester function, or at least one amide function, or at least one amine function,
step f) being carried out, either at the same time as sub-step d1) of step d), or before or after step d), but before step g), it being understood that when step f) is carried out before or after step d), then said step f) includes drying of the catalyst precursor at a temperature below 250° C. after bringing the support into contact with said solution comprising at least one organic compound;
g) the catalyst precursor resulting from steps a) to f) is reduced by bringing said catalyst precursor into contact with a reducing gas at a temperature above or equal to 150° C. and below 250° C.

Advantageously, the mole ratio between said organic compound introduced in step f) and the nickel element also introduced in step d1) is between 0.01 and 5.0 mol/mol.

Advantageously, steps d1) and f) are carried out at the same time.

Advantageously, the organic compound of step f) is chosen from oxalic acid, malonic acid, glycolic acid, lactic acid, tartronic acid, citric acid, tartaric acid, pyruvic acid, levulinic acid, ethylene glycol, propane-1,3-diol, butane-1,4-diol, glycerol, xylitol, mannitol, sorbitol, glycol, glucose, dimethyl carbonate, diethyl carbonate, formamide, N-methylformamide, acetamide, N-methylacetamide, N,N-dimethylmethanamide, 2-pyrrolidone, γ-lactam, lactamide, urea, alanine, arginine, lysine, proline, serine, EDTA. Advantageously, the copper precursor is chosen from copper acetate, copper acetylacetonate, copper nitrate, copper sulfate, copper chloride, copper bromide, copper iodide or copper fluoride.

Advantageously, in step d3), the organic additive is chosen from formic acid, formaldehyde, acetic acid, citric acid, oxalic acid, glycolic acid, malonic acid, ethanol, methanol, ethyl formate, methyl formate, paraldehyde, acetaldehyde, gamma-valerolactone, glucose, sorbitol and trioxane.

Advantageously, the mole ratio between the organic additive introduced in step d2) and the nickel is between 0.1 and 5 mol/mol.

Advantageously, the organic compound of step f) is different from the organic additive of step d2).

Another subject according to the invention relates to a process for the selective hydrogenation of polyunsaturated compounds containing at least 2 carbon atoms per molecule, contained in a hydrocarbon feedstock having a final boiling point below or equal to 300° C., which process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst according to the invention.

Another subject according to the invention relates to a process for the hydrogenation of at least one aromatic or polyaromatic compound contained in a hydrocarbon feedstock having a final boiling point below or equal to 650° C., said process being carried out in the gas phase or in the liquid phase, at a temperature of between 30° C. and 350° C., at a pressure of between 0.1 and 20 MPa, at a hydrogen/(aromatic compounds to be hydrogenated) mole ratio of between 0.1 and 10 and at an hourly space velocity HSV of between 0.05 and 50 $h^{-1}$, in the presence of a catalyst according to the invention.

BRIEF DESCRIPTION OF THE DRAWING

FIG. 1 is a diagram showing the distribution of nickel in the catalyst. The x-axis corresponds to the thickness of the catalyst, measured from the edge of the catalyst (in μm). The y-axis corresponds to the nickel density (in grams of Ni/mm³). The nickel is distributed both on a crust at the periphery of the support, of thickness ep1, and in the core of the support. The nickel density on the crust $d_{crust}$ is greater than the nickel density in the core of the support $d_{core}$. The transition interval between the core and the crust of the catalyst has a thickness denoted ep2-ep1.

DETAILED DESCRIPTION OF THE INVENTION

1. Definitions

In the text hereinbelow, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals of columns 8, 9 and 10 according to the new IUPAC classification.

In the present description, according to the IUPAC convention, "micropores" are understood to mean pores having a diameter of less than 2 nm, i.e. 0.002 μm; "mesopores" are understood to mean pores having a diameter of greater than or equal to 2 nm, i.e. 0.002 μm, and less than or equal to 50 nm, i.e. 0.05 μm, and "macropores" are understood to mean pores having a diameter of greater than 50 nm, i.e. 0.05 μm.

In order to analyze the distribution of the metallic phase on the support, a crust thickness is measured by Castaing microprobe (or electron microprobe microanalysis). The device used is a CAMECA XS100, equipped with four monochromator crystals allowing the simultaneous analysis of four elements. The Castaing microprobe analysis technique consists of the detection of X-rays emitted by a solid after excitation of its elements by a high-energy electron beam. For the purposes of this characterization, the catalyst grains are coated in blocks of epoxy resin. These blocks are polished until the cross section through the diameter of the beads or extrudates is reached, and then metallized by depositing carbon in a metal evaporator. The electron probe is scanned along the diameter of five beads or extrudates to obtain the mean distribution profile of the constituent elements of the solids. This method, well known to those skilled in the art, is defined in the publication by L. Sorbier et al. "*Measurement of palladium crust thickness on catalyst by EPMA*", Materials Science and Engineering 32 (2012). It makes it possible to establish the distribution profile of a given element, here nickel, within the grain. Furthermore, the Ni concentration is defined for each measurement and therefore for each analysis step. The density of Ni within the grain is therefore defined as the concentration of Ni per mm³.

The total pore volume is measured by mercury porosimetry according to the standard ASTM D4284-92 with a wetting angle of 140°, for example using an Autopore III™ model device from the brand Micromeritics™.

The BET specific surface area is measured by nitrogen physisorption according to the standard ASTM D3663-03, a method described in the work by Rouquerol F., Rouquerol J. and Singh K., "*Adsorption by Powders & Porous Solids: Principles, Methodology and Applications*", Academic Press, 1999).

The median mesopore diameter is also defined as being the diameter such that all the pores, among the combined pores constituting the mesopore volume, with a size of less than this diameter constitute 50% of the total mesopore volume determined by intrusion with a mercury porosimeter.

"Size of the nickel particles" is understood to mean the diameter of the nickel crystallites in oxide form. The diameter of the nickel crystallites in oxide form is determined by X-ray diffraction, from the width of the diffraction line located at the angle 2θ=43° (i.e. along the crystallographic direction [200]) using the Scherrer relationship. This method, used in X-ray diffraction on polycrystalline samples or powders, which links the full width at half maximum of the diffraction peaks to the size of the particles, is described in detail in the reference: Appl. Cryst. (1978), 11, 102-113, "Scherrer after sixty years: A survey and some new results in the determination of crystallite size", J. I. Langford and A. J. C. Wilson.

The content of nickel and copper is measured by X-ray fluorescence.

2. Catalyst

The invention relates to a catalyst based on nickel and copper, in a proportion of 1% and 50% by weight of nickel element relative to the total weight of the catalyst, and of 0.5% to 15% by weight of copper element relative to the total weight of the catalyst, and an alumina support, said catalyst being characterized in that:
- the nickel is distributed both on a crust at the periphery of the support, and in the core of the support, the crust thickness (also referred to as ep1) being between 2% and 15% of the diameter of the catalyst, preferably between 2.5% and 12% of the diameter of the catalyst, even more preferably between 3% and 10% of the diameter of the catalyst and even more preferably between 3% and 7.5% of the diameter of the catalyst;
- the nickel density ratio between the crust and the core (also referred to here as $d_{crust}/d_{core}$) is strictly greater than 3, preferably greater than 3.5 and preferably between 3.8 and 15;
- said crust comprises more than 25% by weight of nickel element relative to the total weight of nickel contained in the catalyst, preferably more than 40% by weight, more preferentially between 45% and 90% by weight, and even more preferably between 60% and 90% by weight;
- the mole ratio between the nickel and the copper is between 0.5 and 5 mol/mol, preferably between 0.7 and 4.5 mol/mol, more preferentially between 0.9 and 4 mol/mol;
- at least one portion of the nickel and the copper is in the form of a nickel-copper alloy, advantageously corresponding to the formula $Ni_xCu_y$, with x between 0.1 and 0.9 and y between 0.1 and 0.9;
- the nickel content included in the copper-nickel alloy is between 0.5% and 15% by weight of nickel element relative to the total weight of the catalyst, preferably between 1% and 12% by weight, and more preferentially between 1% and 10% by weight;
- the size of the nickel particles, measured in oxide form, in the catalyst is less than 7 nm, preferably less than 5 nm, more preferentially less than 4 nm, and even more preferentially less than 3 nm.

Advantageously, the transition interval between the core and the crust of the catalyst (also referred to here as the core/crust transition interval, or ep2-ep1 according to the notations in FIG. 1), linked to the variation in the nickel density measured over the thickness of the catalyst from the edge of the catalyst to the center of the catalyst, is very abrupt. Preferably, the core/crust transition interval is between 0.05% and 3% of the diameter of the catalyst, preferably between 0.5% and 2.5% of the diameter of the catalyst.

The nickel content in said catalyst according to the invention is advantageously between 1% and 50% by weight relative to the total weight of the catalyst, more preferentially between 2% and 40% by weight and even more preferentially between 3% and 35% by weight and even more preferentially 5% and 25% by weight relative to the total weight of the catalyst.

The copper content is between 0.5% and 15% by weight of copper element relative to the total weight of the catalyst, preferably between 0.5% and 12% by weight, preferably between 0.75% and 10% by weight, and even more preferentially between 1% and 9% by weight.

The catalyst according to the invention can be described as a "semi eggshell" catalyst in which the concentration of nickel is higher at the periphery of the support than in the core of the support, said concentration of nickel in the core of the support being non-zero.

The specific surface area of the catalyst is generally between 10 $m^2/g$ and 200 $m^2/g$, preferably between 25 $m^2/g$ and 110 $m^2/g$, more preferably between 40 $m^2/g$ and 100 $m^2/g$.

The total pore volume of the catalyst is generally between 0.1 and 1 ml/g, preferably between 0.2 ml/g and 0.8 ml/g, and particularly preferably between 0.3 ml/g and 0.7 ml/g.

The active phase of the catalyst does not comprise a metal from Group VIB. In particular, it does not comprise molybdenum or tungsten.

Said catalyst (and the support used for the preparation of the catalyst) is in the form of grains advantageously having a diameter of between 0.5 and 10 mm. The grains may have any form known to those skilled in the art, for example the form of beads (preferably having a diameter of between 1 and 8 mm), of extrudates, of tablets or of hollow cylinders. Preferably, the catalyst (and the support used for the preparation of the catalyst) are in the form of extrudates with a diameter of between 0.5 and 10 mm, preferably between 0.8 and 3.2 mm and very preferably between 1.0 and 2.5 mm and with a length of between 0.5 and 20 mm. The "diameter" of the extrudates is intended to mean the diameter of the circle circumscribed in the cross section of these extrudates. The catalyst can advantageously be presented in the form of cylindrical, multilobate, trilobate or quadrilobate extrudates. Preferably, its shape will be trilobate or quadrilobate. The shape of the lobes could be adjusted according to all the methods known from the prior art.

3. Support

The characteristics of the alumina, mentioned in this section, correspond to the characteristics of the alumina before impregnation of the nickel active phase, i.e. the alumina support obtained at the end of step c) of the process for preparing the catalyst according to the invention.

According to the invention, the support is an alumina, that is to say that the support comprises at least 95%, preferably at least 98%, and particularly preferably at least 99% by weight of alumina relative to the weight of the support. The alumina generally has a crystallographic structure of delta, gamma or theta alumina type, alone or as a mixture.

According to the invention, the alumina support may comprise impurities such as oxides of metals from groups IIA, IIIB, IVB, IIB, IIIA, IVA according to the CAS classification, preferably silica, titanium dioxide, zirconium dioxide, zinc oxide, magnesium oxide and calcium oxide, or else alkali metals, preferably lithium, sodium or potassium, and/or alkaline-earth metals, preferably magnesium, calcium, strontium or barium or else sulfur.

Advantageously, the sulfur content of the alumina support is between 0.001% and 2% by weight relative to the total weight of the alumina support, and the sodium content of said alumina support is between 0.001% and 2% by weight relative to the total weight of said alumina gel.

The specific surface area of the alumina is generally between 10 m$^2$/g and 250 m$^2$/g, preferably between 30 m$^2$/g and 200 m$^2$/g, more preferably between 50 m$^2$/g and 150 m$^2$/g. The pore volume of the alumina is generally between 0.1 ml/g and 1.2 ml/g, preferably between 0.3 ml/g and 0.9 ml/g, and very preferably between 0.5 ml/g and 0.9 ml/g.

Process for Preparing the Catalyst

Another subject according to the invention relates to a process for preparing a catalyst according to the invention, comprising at least the following steps:
a) an alumina gel is provided;
b) the alumina gel from step a) is shaped;
c) the shaped alumina gel obtained at the end of step b) is subjected to a heat treatment comprising at least one hydrothermal treatment step in an autoclave in the presence of an acid solution, at a temperature of between 100° C. and 800° C., and at least one calcining step, at a temperature of between 400° C. and 1500° C., carried out after the hydrothermal treatment step, in order to obtain an alumina support;
d) the sequence of the following sub-steps is carried out:
  d1) the alumina support is brought into contact with at least one precursor of the nickel active phase in order to obtain a catalyst precursor,
  d2) the catalyst precursor obtained at the end of step d1) is dried at a temperature below 250° C.;
  d2') optionally, a heat treatment of the dried catalyst precursor obtained at the end of step d2) is carried out at a temperature of between 250° C. and 1000° C. in order to obtain a calcined catalyst precursor;
  d3) the dried catalyst precursor obtained at the end of step d2) (optionally d2') is brought into contact with at least one solution containing at least one organic additive chosen from aldehydes containing 1 to 14 carbon atoms per molecule, ketones or polyketones containing 3 to 18 carbon atoms per molecule, ethers and esters containing 2 to 14 carbon atoms per molecule, alcohols or polyalcohols containing 1 to 14 carbon atoms per molecule and carboxylic acids or polycarboxylic acids containing 1 to 14 carbon atoms per molecule, the mole ratio between the organic additive and the nickel being greater than 0.05 mol/mol;
  d4) a hydrothermal treatment of the catalyst precursor obtained at the end of step d3) is carried out at a temperature between 100° C. and 200° C. for a period of between 30 minutes and 5 hours under a gas stream comprising between 5 and 650 grams of water per kg of dry gas;
  d5) optionally, a step of drying the catalyst precursor obtained at the end of step d4) between 50° C. and 200° C. is carried out under a gas stream comprising an amount of water strictly less than 5 grams of water per kilogram of dry gas;
e) the sequence of the following sub-steps is carried out:
  e1) the alumina support is brought into contact with at least one solution containing at least one copper precursor and one nickel precursor at a desired nickel concentration in order to obtain, on the final catalyst, a content of between 0.5% and 15% by weight of nickel element relative to the total weight of the final catalyst;
  e2) at least one step of drying the catalyst precursor obtained at the end of step e1) is carried out at a temperature below 250° C.;
  e3) optionally, a heat treatment of the catalyst precursor obtained at the end of step e2) is carried out at a temperature of between 250° C. and 1000° C., in the presence or absence of water;
steps d) and e) being carried out separately in any order,
f) the alumina support is brought into contact with at least one solution containing at least one organic compound comprising at least one carboxylic acid function, or at least one alcohol function, or at least one ester function, or at least one amide function, or at least one amine function,
step f) being carried out, either at the same time as sub-step d1) of step d), or before or after step d), but before step g), it being understood that when step f) is carried out before or after step d), then said step f) includes drying of the catalyst precursor at a temperature below 250° C. after bringing the support into contact with said solution comprising at least one organic compound;
g) the catalyst precursor resulting from steps a) to f) is reduced by bringing said catalyst precursor into contact with a reducing gas at a temperature above or equal to 150° C. and below 250° C.

Intermediate steps can be inserted (in particular additional drying steps) and certain steps can be carried out several times in a row (for example step d1). Finally, it is possible to add additional steps before using the catalyst at the end of step g).

Preferably, a step of drying and then of calcining is carried out at the end of the shaping step b) (but before carrying out step c).

Preferably, steps d2') and d5) are not optional.

Steps a) to g) of said preparation process are described in detail below.

Step a)—Alumina Gel

The catalyst according to the invention comprises an alumina support which is obtained from an alumina gel which essentially comprises a precursor of aluminum oxy (hydroxide) (AlO(OH)) type—also known as boehmite.

According to the invention, the alumina gel (or otherwise known as boehmite gel) is synthesized by precipitation of basic and/or acidic solutions of aluminum salts induced by a change in pH or any other method known to those skilled in the art (P. Euzen, P. Raybaud, X. Krokidis, H. Toulhoat, J. L. Le Loarer, J. P. Jolivet and C. Froidefond, Alumina, in "Handbook of Porous Solids", edited by F. Schüth, K. S. W. Sing and J. Weitkamp, Wiley-VCH, Weinheim, Germany, 2002, pp. 1591-1677).

Generally the precipitation reaction is carried out at a temperature of between 5° C. and 80° C., and at a pH of between 6 and 10. Preferably, the temperature is between 35° C. and 70° C. and the pH is between 6 and 10.

According to one embodiment, the alumina gel is obtained by bringing an aqueous solution of an acid salt of aluminum into contact with a basic solution. For example, the acid salt of aluminum is chosen from the group consisting of aluminum sulfate, aluminum nitrate or aluminum chloride and preferably said acid salt is aluminum sulfate. The basic solution is preferentially chosen from sodium hydroxide or potassium hydroxide.

Alternatively, an alkaline solution of aluminum salts which may be chosen from the group consisting of sodium aluminate and potassium aluminate may be brought into contact with an acid solution. In a very preferred variant, the gel is obtained by bringing a sodium aluminate solution into contact with nitric acid. The sodium aluminate solution advantageously has a concentration of between $10^{-5}$ and $10^{-1}$ mol·L$^{-1}$ and preferably this concentration is between $10^{-4}$ and $10^{-2}$ mol·L$^{-1}$.

According to another embodiment, the alumina gel is obtained by bringing an aqueous solution of acid salts of aluminum into contact with an alkaline solution of aluminum salts.

Step b)—Shaping of the Support

The support may advantageously be shaped by any technique known to those skilled in the art. The shaping may be carried out for example by kneading-extrusion, by pelletizing, by the drop coagulation (oil-drop) method, by granulation on a rotating plate or by any other method that is well known to those skilled in the art. The catalysts according to the invention can optionally be manufactured and used in the form of extrudates, tablets, beads. The advantageous shaping method according to the invention is extrusion and the preferred extrudate shapes are cylindrical, twisted cylindrical or multilobate (2, 3, 4 or 5 lobes for example).

In a particular embodiment, the alumina gel obtained at the end of step a) is subjected to a step of kneading, preferably in an acidic medium. The acid used may for example be nitric acid. This step is carried out by means of known tools such as Z-arm mixers, grinding mixers, continuous single or twin screws that enable the gel to be converted into a product having the consistency of a paste. According to one advantageous embodiment, one or more compounds referred to as "pore-forming agents" are introduced into the kneading medium. These compounds have the property of degrading on heating and thus creating porosity in the support. For example, wood flour, charcoal, tars and plastics can be used as pore-forming compounds. The paste thus obtained after kneading is passed through an extrusion die. Generally the extrudates have a diameter of between 0.5 and 10 mm, preferably between 0.8 and 3.2 mm and very preferably between 1.0 and 2.5 mm and a length of between 0.5 and 20 mm. These extrudates can be cylindrical, multilobate (for example trilobate or quadrilobate).

After the shaping thereof, the support is optionally dried before undergoing the hydrothermal treatment according to step c) of the process. For example, the drying is carried out at a temperature between 50° C. and 200° C. The dried support is optionally calcined before undergoing the hydrothermal treatment according to step c) of the process. For example, the calcining is carried out at a temperature between 200° C. and 1000° C., in the presence or absence of a stream of air containing up to 150 grams of water per kilogram of dry air.

Step c)—Heat Treatment

The support obtained at the end of step b) then undergoes a heat treatment step which makes it possible to give it physical properties that satisfy the envisaged application.

The term "hydrothermal treatment" denotes a treatment by passing through an autoclave in the presence of water at a temperature above room temperature.

During this hydrothermal treatment, the shaped alumina can be treated in different ways. Thus, the alumina can be impregnated with an acid solution, prior to passing through the autoclave, it being possible for the hydrothermal treatment of the alumina to be carried out either in the vapor phase or in the liquid phase, it being possible for this vapor or liquid phase of the autoclave to be acidic or non-acidic. This impregnation, prior to the hydrothermal treatment, may be performed dry or by immersing the alumina in an acidic aqueous solution. The term "dry impregnation" means placing the alumina in contact with a volume of solution less than or equal to the total pore volume of the treated alumina. Preferably, the impregnation is performed dry.

It is also possible to treat the extruded support without prior impregnation with an acidic solution, the acidity in this case being provided by the aqueous liquid of the autoclave.

The acidic aqueous solution comprises at least one acidic compound for dissolving at least one portion of the alumina of the extrudates. The term "acidic compound for dissolving at least one portion of the alumina of the extrudates" is understood to mean any acidic compound which, brought into contact with the alumina extrudates, dissolves at least one portion of the aluminum ions. The acid should preferably dissolve at least 0.5% by weight of alumina of the alumina extrudates.

Preferably, this acid is chosen from strong acids such as nitric acid, hydrochloric acid, perchloric acid, sulfuric acid or a weak acid used at a concentration such that its aqueous solution has a pH of less than 4, such as acetic acid, or a mixture of these acids.

According to a preferred embodiment, the hydrothermal treatment is carried out in the presence of nitric acid and acetic acid taken alone or as a mixture. The autoclave is preferably a rotating basket autoclave, such as the one defined in patent application EP-A-0 387 109.

The hydrothermal treatment may also be carried out under saturation vapor pressure or under a partial pressure of water vapor at least equal to 70% of the saturation vapor pressure corresponding to the treatment temperature.

Preferably the hydrothermal treatment is conducted at a temperature of between 100° C. and 800° C., preferably between 200° C. and 700° C., preferably between 30 minutes and 8 hours, more preferentially between 30 minutes and 3 hours.

Preferably, the calcining step which takes place after the hydrothermal treatment in the autoclave takes place at a temperature generally of between 400° C. and 1500° C., preferably between 800° C. and 1300° C., preferably for 1 and 5 hours in air, the water content of which is generally between 0 and 700 g of water per kilogram of dry air.

At the end of step c), the alumina obtained exhibits the specific textural properties as described above.

Step d)

Step d) comprises the following sub-steps.

Step d1)—Bringing the Support into Contact with a Precursor of the Nickel Active Phase The support may be brought into contact with a solution containing a precursor of the nickel active phase, in accordance with the implementation of step d1), by dry impregnation or excess impregnation, or else by deposition-precipitation, according to methods well known to those skilled in the art.

Said step d1) is preferentially carried out by impregnation of the support consisting, for example, of bringing the support into contact with at least one aqueous solution containing a nickel precursor. The pH of said solution could be modified by the optional addition of an acid or of a base.

Preferably, said step d1) is carried out by dry impregnation, which consists in bringing the support into contact with at least one solution containing, preferably consisting of, at least one nickel precursor, the volume of the solution of which is between 0.25 and 1.5 times the pore volume of the support to be impregnated.

Preferably, said nickel precursor is introduced in aqueous solution, for example in nitrate, carbonate, acetate, chloride or oxalate form, in the form of complexes formed by a polyacid or an acid alcohol and its salts, in the form of complexes formed with acetylacetonates or in the form of any other inorganic derivative soluble in aqueous solution, which is brought into contact with said support. Preferably, use is advantageously made, as nickel precursor, of nickel nitrate, nickel chloride, nickel acetate or nickel hydroxycarbonate. Very preferably, the nickel precursor is nickel nitrate.

According to another variant, the aqueous solution may contain aqueous ammonia or ammonium $NH_4^+$ ions.

The concentration of nickel in solution is adjusted depending on the type of impregnation (dry impregnation or excess impregnation) and the pore volume of the support so as to obtain, for the supported catalyst, a nickel content of between 1% and 50% by weight of nickel element relative to the total weight of the catalyst, more preferentially between 2% and 40% by weight and even more preferentially between 3% and 35% by weight and even more preferentially 5% and 25% by weight.

Step d2)—Drying

The drying step is carried out under a gas stream comprising an amount of water of less than 150 grams of water per kilogram of dry gas, preferably less than 50 g of water per kilogram of dry gas, at a temperature below 250° C., preferably between 15° C. and 240° C., more preferentially between 30° C. and 220° C., more preferentially still between 50° C. and 200° C., and even more preferentially between 70° C. and 180° C., for a period typically of between 10 minutes and 24 hours. Longer periods of time are not ruled out, but do not necessarily provide any improvement.

The gas may contain oxygen, nitrogen or an inert gas and preferably the gas is air.

Step d2')—Calcining (Optional)

The optional calcining step is carried out under a gas stream comprising an amount of water of less than 150 grams of water per kilogram of dry gas, preferably less than 50 g of water per kilogram of dry gas, at a temperature of between 250° C. and 1000° C., preferably between 250° C. and 750° C. The duration of this heat treatment is generally between 15 minutes and 10 hours. Longer periods of time are not ruled out, but do not necessarily provide any improvement.

The gas may contain oxygen, nitrogen or an inert gas and preferably the gas is air.

At the end of steps d2) or d2'), the nickel is distributed homogeneously on the support.

Step d3)—Additive

According to step d3) of the process for preparing the catalyst, the catalyst precursor obtained at the end of step d2), optionally at the end of step d2'), is brought into contact with at least one solution comprising at least one organic additive chosen from aldehydes containing from 1 to 14 (preferably from 2 to 12) carbon atoms per molecule, ketones or polyketones containing from 3 to 18 (preferably from 3 to 12) carbon atoms per molecule, ethers or esters containing from 2 to 14 (preferably from 3 to 12) carbon atoms per molecule, alcohols or polyalcohols containing from 1 to 14 (preferably from 2 to 12) carbon atoms per molecule and carboxylic acids or polycarboxylic acids containing from 1 to 14 (preferably from 1 to 12) carbon atoms per molecule. The organic additive may be composed of a combination of the various functional groups mentioned above.

Preferably, the organic additive is chosen from formic acid HCOOH, formaldehyde $CH_2O$, acetic acid $CH_3COOH$, citric acid, oxalic acid, glycolic acid (HOOC—$CH_2$—OH), malonic acid (HOOC—$CH_2$—COOH), ethanol, methanol, ethyl formate $HCOOC_2H_5$, methyl formate $HCOOCH_3$, paraldehyde $(CH_3—CHO)_3$, acetaldehyde $C_2H_4O$, gamma-valerolactone $(C_5H_8O_2)$, glucose, sorbitol and trioxane.

Particularly preferably, the organic additive is formic acid.

It is essential that the step of adding the organic additive to the catalyst (step d3)) is carried out after the step of bringing the support into contact with the precursor of the nickel active phase.

Preferably, said step d3) is carried out by impregnating the catalyst precursor obtained at the end of the implementation of step d2) or of step d2') with a solution comprising at least one organic additive as mentioned above. The impregnation is generally carried out in aqueous solution or in organic solution or in suspension in aqueous or organic solution, preferably in aqueous solution. When the operation is carried out in organic solution or suspension, an alcohol or polyalcohol, glycol or polyglycol will preferably be used as organic solvent.

Preferably, said step d3) is carried out by dry impregnation, which consists in bringing the catalyst precursor obtained at the end of the implementation of step d2) or of step d2') into contact with a solution comprising at least one organic additive as mentioned above, the volume of the solution of which is between 0.25 and 1.5 times the pore volume of the catalyst precursor to be impregnated.

The impregnation is generally carried out at a temperature between 0° C. and 50° C., preferably between 10° C. and 40° C., and particularly preferably at room temperature.

According to the invention, the mole ratio between the organic additive and the nickel is greater than 0.05 mol/mol, preferably between 0.1 and 5 mol/mol, more preferentially between 0.12 and 3 mol/mol, and even more preferably between 0.15 and 2.5 mol/mol.

Step d4)—Hydrothermal Treatment

According to step d4) of the process for preparing the catalyst according to the invention, a hydrothermal treatment of the product resulting from step d3) is carried out at a temperature of between 100° C. and 200° C., preferably between 130° C. and 170° C., and more particularly around 150° C., under a gas stream comprising between 5 and 650 grams of water per kilogram of dry gas, preferably between 7 and 150 grams of water per kilogram of dry gas, even more preferably between 10 and 50 grams of water per kilogram of dry gas. The gas may contain oxygen, nitrogen or an inert gas and preferably the gas is air.

The duration of the hydrothermal treatment is generally between 30 minutes and 5 hours, preferably between 1 to 3 hours.

Step d5)—Drying (Optional)

Step d4) can be followed by a step d5) of drying between 50° C. and 200° C. under a gas stream comprising an amount of water strictly less than 5 grams of water per kilogram of dry gas, advantageously for a time of between 30 minutes and 5 hours, preferably between 1 to 3 hours. The gas may contain oxygen, nitrogen or an inert gas and preferably the gas is air.

At the end of step d4), or optionally of step d5), a "semi eggshell" catalyst is obtained as shown schematically in FIG. 1 and the characteristics of which are described above.

Step e)

Step e) comprises the following sub-steps.

Step e1) Bringing a Precursor of Copper and Nickel into Contact with the Support The deposition of nickel and copper on the alumina support may be carried out by dry impregnation or excess impregnation, or also by deposition-precipitation, according to methods well known to those skilled in the art.

Said step e1) is preferentially carried out by impregnation of the catalyst precursor consisting for example in bringing said support into contact with at least one solution, which is aqueous or organic (for example methanol or ethanol or phenol or acetone or toluene or dimethyl sulfoxide (DMSO)) or else consists of a mixture of water and at least one organic solvent, comprising, preferably consisting of, at least one nickel precursor and at least one copper precursor at least partially in the dissolved state, or else in bringing said catalyst precursor into contact with at least one colloidal solution comprising, preferably consisting of, at least one nickel precursor and one copper precursor in oxidized form (nanoparticles of oxide, of oxy(hydroxide) or of hydroxide of nickel and copper) or in reduced form (metallic nanoparticles of nickel and copper in the reduced state). Preferably, the solution is aqueous. The pH of this solution may be modified by the optional addition of an acid or of a base.

Preferably, said step e1) is carried out by dry impregnation, which consists in bringing the support of the catalyst precursor into contact with a solution comprising, preferably consisting of, at least one nickel precursor and at least one copper precursor, the volume of the solution of which is between 0.25 and 1.5 times the pore volume of the support to be impregnated.

When the nickel precursor is introduced in aqueous solution, use is advantageously made of a nickel precursor in the nitrate, carbonate, acetate, chloride, hydroxide, hydroxycarbonate, oxalate, sulfate or formate form, in the form of complexes formed by a polyacid or an acid alcohol and its salts, in the form of complexes formed with acetylacetonates, in the form of tetrammine or hexammine complexes, or else in the form of any other inorganic derivative soluble in aqueous solution, which is brought into contact with said catalyst precursor. Preferably, nickel nitrate, nickel hydroxide, nickel carbonate, nickel chloride or nickel hydroxycarbonate is advantageously used as nickel precursor. Very preferably, the nickel precursor is nickel nitrate, nickel carbonate or nickel hydroxide.

When the copper precursor is introduced in aqueous solution, a copper precursor in mineral or organic form is advantageously used. In mineral form, the copper precursor can be chosen from copper acetate, copper acetylacetonate, copper nitrate, copper sulfate, copper chloride, copper bromide, copper iodide or copper fluoride. Very preferably, the copper precursor salt is copper nitrate.

According to the invention, the nickel precursor is supplied in step e1) at a desired concentration in order to obtain on the final catalyst (i.e. obtained at the end of the reduction step f) or the passivation step g) if the latter is carried out) a content of between 0.5% and 10% by weight of nickel element relative to the total weight of the final catalyst, preferably between 0.5% and 8% by weight, more preferentially between 1% and 7% by weight, even more preferentially between 1% and 5% by weight.

The amounts of the copper precursor(s) introduced into the solution according to step e1) are chosen such that the total copper content is between 0.5% and 15% by weight of copper element relative to the total weight of the final catalyst (i.e. obtained at the end of the reduction step f) or the passivation step g) if the latter is carried out), preferably between 0.5% and 12% by weight, preferably between 0.75% and 10% by weight, and even more preferentially between 1% and 9% by weight.

Step e2) Drying the Impregnated Support

Step e2) of drying the impregnated support is carried out at a temperature of less than 250° C., preferably of between 15° C. and 180° C., more preferentially between 30° C. and 160° C., even more preferentially between 50° C. and 150° C., and even more preferentially between 70° C. and 140° C., for a period typically of between 10 minutes and 24 hours. Longer periods of time are not ruled out, but do not necessarily provide any improvement.

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or nitrogen.

Step e3) Heat Treatment of the Dried Catalyst (Optional Step)

The dried catalyst precursor can undergo an additional heat treatment step, before the reduction step f), at a temperature of between 250° C. and 1000° C. and preferably between 250° C. and 750° C., for a period typically between 15 minutes and 10 hours, under an inert atmosphere or under an oxygen-containing atmosphere, optionally in the presence of water. Longer treatment times are not ruled out but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed. After this or these treatment(s), the catalyst precursor comprises nickel in the oxide form, that is to say in the NiO form.

In the event of water being present, the water content is preferably between 150 and 900 grams per kilogram of dry air and even more preferably between 250 and 650 grams per kilogram of dry air.

Implementation of Step e) in Relation to the Other Steps of the Preparation Process The process for the preparation of the nickel catalyst comprises several embodiments. They differ in particular by the order of introduction of the nickel and copper precursors constituting the NiCu alloy. It is possible for the nickel and copper precursors to be brought into contact with the support either after the nickel precursor has been brought into contact with the support, or before the nickel precursor is brought into contact with the support.

A first embodiment consists in carrying out said step e) prior to said step d).

A second embodiment consists in carrying out said step d) prior to said step e).

When step e) is carried out before or after step d), said step e) includes drying the catalyst precursor at a temperature below 250° C. after bringing the support into contact with said solution comprising at least one organic compound.

Step f) Addition of the Organic Compound

Said support may be bought into contact with at least one solution containing at least one organic compound comprising at least one carboxylic acid function, or at least one alcohol function, or at least one ester function, or at least one amide function, or at least one amine function in accordance with the implementation of said step f), by any method well known to those skilled in the art. This is because it has in addition been noticed that the catalysts according to the invention prepared in the presence of an organic compound (from among those mentioned above) are more active than the catalysts prepared in the absence of this type of organic compound. This effect is related to the decrease in the size of the nickel particles.

In particular, said step f) may be carried out by dry impregnation or by excess impregnation according to methods well known to those skilled in the art. Preferably, said step f) is carried out by dry impregnation, which consists in bringing the support of the catalyst into contact with a volume of said solution of between 0.25 and 1.5 times the pore volume of the support to be impregnated.

Said solution containing at least one organic compound comprising at least one carboxylic acid function, or at least one alcohol function, or at least one ester function, or at least one amide function, or at least one amine function, may be aqueous or organic (for example methanol or ethanol or phenol or acetone or toluene or dimethyl sulfoxide (DMSO)) or else consist of a mixture of water and of at least one organic solvent. Said organic compound is, beforehand, at least partially dissolved in said solution at the desired concentration. Preferably, said solution is aqueous or contains ethanol. More preferably still, said solution is aqueous. The pH of said solution could be modified by the optional addition of an acid or of a base. In another possible embodiment, the solvent may be absent from the impregnation solution.

In the embodiment in which step f) is carried out by dry impregnation or excess impregnation, preferably dry impregnation, the impregnation of the support with at least one solution containing at least said organic compound may advantageously be carried out via at least two impregnation cycles, using identical or different organic compounds in each cycle. In this case, each impregnation is advantageously followed by drying and optionally a heat treatment.

Advantageously, the mole ratio of said organic compound introduced in step f) to the nickel element also introduced in step d1) is between 0.01 and 5.0 mol/mol, preferably between 0.05 and 2.0 mol/mol, more preferentially between 0.1 and 1.5 mol/mol and more preferentially still between 0.3 and 1.2 mol/mol.

The organic compound according to step f) may comprise, within the same molecule, several, identical or different, carboxylic acid, alcohol, ester, amide or amine organic functions. The organic compound according to step f) may comprise a combination of several organic functions chosen from carboxylic acid, alcohol, ester, amide or amine organic functions.

Preferably, the organic compound of step f) is different from the organic additive of step d2).

A) Organic Compound Comprising at Least One Carboxylic Acid Function

In one embodiment according to the invention, the organic compound comprises at least one carboxylic acid function.

Said organic compound comprising at least one carboxylic acid function may be a saturated or unsaturated aliphatic organic compound or an aromatic organic compound. Preferably, the saturated or unsaturated aliphatic organic compound comprises between 1 and 9 carbon atoms, preferably between 2 and 7 carbon atoms. Preferably, the aromatic organic compound comprises between 7 and 10 carbon atoms, preferably between 7 and 9 carbon atoms.

Said saturated or unsaturated aliphatic organic compound or said aromatic organic compound comprising at least one carboxylic acid function may be chosen from monocarboxylic acids, dicarboxylic acids, tricarboxylic acids or tetracarboxylic acids.

Advantageously, the organic compound comprising at least one carboxylic acid function is chosen from ethanedioic acid (oxalic acid), propanedioic acid (malonic acid), pentanedioic acid (glutaric acid), hydroxyacetic acid (glycolic acid), 2-hydroxypropanoic acid (lactic acid), 2-hydroxypropanedioic acid (tartronic acid), 2-hydroxypropane-1,2,3-tricarboxylic acid (citric acid), 2,3-dihydroxybutanedioic acid (tartaric acid), 2-oxopropanoic acid (pyruvic acid) or 4-oxopentanoic acid (levulinic acid).

B) Organic Compound Comprising at Least One Alcohol Function

In another embodiment according to the invention, the organic compound comprises at least one alcohol function.

Preferably, said organic compound comprises between 2 and 20 carbon atoms, preferably between 2 and 12 carbon atoms and more preferably still between 2 and 8 carbon atoms.

Advantageously, the organic compound is chosen from methanol, ethanol, phenol, ethylene glycol, propane-1,3-diol, butane-1,4-diol, pentane-1,5-diol, hexane-1,6-diol, glycerol, xylitol, mannitol, sorbitol, pyrocatechol, resorcinol, hydroquinone, diethylene glycol, triethylene glycol, polyethylene glycols having an average molar mass of less than 600 g/mol, glucose, mannose, fructose, sucrose, maltose or lactose, in any one of the isomeric forms thereof.

C) Organic Compound Comprising at Least One Ester Function

In another embodiment according to the invention, the organic compound comprises at least one ester function.

Preferably, said organic compound comprises between 2 and 20 carbon atoms, preferably between 3 and 14 carbon atoms and more preferentially still between 3 and 8 carbon atoms.

Said organic compound may be chosen from a linear or cyclic or unsaturated cyclic carboxylic acid ester, or a cyclic or linear carbonic acid ester, or else a linear carbonic acid diester. In the case of a carboxylic acid cyclic ester, said compound is γ-valerolactone.

In the case of a carboxylic acid unsaturated cyclic ester (containing unsaturations in the ring), the compound can be furan or pyrone or any one of their derivatives, such as 6-pentyl-α-pyrone.

In the case of a carboxylic acid linear ester, the compound may be a compound comprising a single ester function corresponding to the empirical formula RCOOR', in which R and R' are linear, branched or cyclic alkyl groups, or alkyl groups containing unsaturations, or alkyl groups substituted by one or more aromatic rings, or aryl groups, each containing between 1 and 15 carbon atoms and which may be identical or different. The R group can also be the hydrogen atom H. Said organic compound is preferably methyl laurate.

In another embodiment according to the invention, the organic compound may be a compound comprising at least two carboxylic acid ester functions. Preferably, said compound is dimethyl succinate.

In another embodiment according to the invention, the organic compound may be a compound comprising at least one carboxylic acid ester function and at least one second functional group chosen from alcohols, ethers, ketones or aldehydes.

Preferably, said compound is dimethyl malate.

Advantageously, said organic compound comprises at least one carboxylic acid ester function and at least one ketone or aldehyde function. In the case of a carbonic acid cyclic ester, the compound is propylene carbonate. In the case of a carbonic acid linear ester, the compound is chosen from dimethyl carbonate, diethyl carbonate or diphenyl carbonate. In the case of a carbonic acid linear diester, the compound is chosen from dimethyl dicarbonate, diethyl dicarbonate or di(tert-butyl) dicarbonate.

D) Organic Compound Comprising at Least One Amide Function

In another embodiment according to the invention, the organic compound comprises at least one amide function chosen from an acyclic amide function or a cyclic amide function optionally comprising alkyl substituents, aryl substituents or alkyl substituents containing unsaturations. The amide functions can be chosen from primary, secondary or tertiary amides.

Advantageously, the organic compound comprising at least one amide function is chosen from formamide, N-methylformamide, N,N-dimethylformamide, N-ethylformamide, N,N-diethylformamide, acetamide, N-methylacetamide, N,N-dimethylmethanamide, N,N-diethylacetamide, N,N-dimethylpropionamide, propanamide, 2-pyrrolidone, N-methyl-2-pyrrolidone, γ-lactam, caprolactam, acetylleucine, N-acetylaspartic acid, aminohippuric acid, N-acetylglutamic acid, 4-acetamidobenzoic acid, lactamide and glycolamide, urea, N-methylurea, N,N'-dimethylurea, 1,1-dimethylurea, and tetramethylurea, in any one of the isomeric forms thereof.

E) Organic Compound Comprising at Least One Amine Function

In another embodiment according to the invention, the organic compound comprises at least one amine function. Said organic compound comprises between 1 and 20 carbon atoms, preferably between 1 and 14 carbon atoms and more preferably still between 2 and 8 carbon atoms.

In one embodiment according to the invention, said organic compound comprising at least one amine function corresponding to the empirical formula $C_xN_yH_z$ in which $1 \leq x \leq 20$, $1 \leq y \leq x$, $2 \leq z \leq 2x+2$. More particularly, the organic compound is chosen from ethylenediamine, diaminohexane, tetramethylenediamine, hexamethylenediamine, tetramethylethylenediamine, tetraethylethylenediamine, diethylenetriamine and triethylenetetramine.

In one embodiment according to the invention, said organic compound comprises at least one amine function and at least one carboxylic acid function (amino acid). When the compound is an amino acid, it is preferably chosen from alanine, arginine, lysine, proline, serine, threonine or EDTA.

Among all the above embodiments, the organic compound is chosen from oxalic acid, malonic acid, glycolic acid, lactic acid, tartronic acid, citric acid, tartaric acid, pyruvic acid, levulinic acid, ethylene glycol, propane-1,3-diol, butane-1,4-diol, glycerol, xylitol, mannitol, sorbitol, diethylene glycol, glucose, gamma-valerolactone, dimethyl carbonate, diethyl carbonate, formamide, N-methylformamide, acetamide, N-methylacetamide, N,N-dimethylmethanamide, 2-pyrrolidone, γ-lactam, lactamide, urea, alanine, arginine, lysine, proline, serine, EDTA.

Implementation of Step f) in Relation to the Other Steps of the Preparation Process The process for the preparation of the nickel catalyst comprises several embodiments. They differ in particular in the order of introduction of the organic compound and of the nickel precursor, it being possible for the organic compound to be brought into contact with the support either after the nickel precursor has been brought into contact with the support, or before the nickel precursor is brought into contact with the support, or at the same time as the nickel is bought into contact with the support.

A first embodiment consists in carrying out said step d) prior to said step f).

A second embodiment consists in carrying out said step f) prior to said step d).

When step f) is carried out before or after step d), said step f) includes drying the catalyst precursor at a temperature below 250° C. after bringing the support into contact with said solution comprising at least one organic compound.

Each step of bringing the support into contact with the nickel precursor (step d1) and of bringing the support into contact with at least one solution containing at least one organic compound comprising at least one carboxylic acid function, or at least one alcohol function, or at least one ester function, or at least one amide function or at least one amine function, (step f), is carried out at least once and may advantageously be carried out several times, optionally in the presence of a nickel precursor and/or of an organic compound which is (are) identical or different in each step d1) and/or f) respectively.

A third embodiment consists in carrying out said step d1) and said step f) simultaneously (co-contacting). This embodiment can advantageously comprise the implementation of one or more steps d1), optionally with an identical or different nickel precursor in each step d1). In particular, one or more steps d1) precede and/or advantageously follow said co-contacting step, optionally with an identical or different nickel precursor in each step. This embodiment may comprise several co-contacting steps: steps d1) and f) are carried out simultaneously several times, optionally in the presence of a nickel precursor and/or of an organic compound which is (are) identical or different in each co-contacting step.

Each contacting step can preferably be followed by an intermediate drying step. The intermediate drying step is carried out at a temperature below 250° C., preferably of between 15 and 240° C., more preferably between 30 and 220° C., more preferably still between 50 and 200° C. and in an even more preferred way between 70 and 180° C. Advantageously, when an intermediate drying step is carried out, an intermediate calcining step may be carried out. The intermediate calcining step is carried out at a temperature of between 250 and 1000° C., preferably between 250 and 750° C.

Advantageously, after each contacting step, whether this is a step of bringing the nickel precursor into contact with the support, a step of bringing the organic compound into contact with the support, or a step of bringing the nickel precursor and the organic compound into contact simultaneously with the support, it is possible to leave the impregnated support to mature, optionally before an intermediate drying step. Maturation makes it possible for the solution to be distributed homogeneously within the support. When a maturing step is carried out, said step is advantageously carried out at atmospheric pressure or at reduced pressure, under an inert atmosphere or under an oxygen-containing atmosphere or under a water-containing atmosphere, and at a temperature of between 10° C. and 50° C. and preferably at ambient temperature. Generally, a maturing time of less than forty-eight hours and preferably of between five minutes and five hours is sufficient. Longer periods of time are not ruled out, but do not necessarily provide any improvement.

Step g) Reduction with a Reducing Gas

Prior to the use of the catalyst in the catalytic reactor and the implementation of a hydrogenation process, a reducing treatment step g) is carried out in the presence of a reducing gas so as to obtain a catalyst comprising nickel at least partially in the metallic form. This step is advantageously carried out in situ, that is to say after charging of the catalyst to a hydrogenation reactor. This treatment makes it possible to activate said catalyst and to form metal particles, in particular of nickel in the zero-valent state. The in situ implementation of the catalyst reducing treatment makes it possible to dispense with an additional step of passivation of the catalyst with an oxygen-bearing compound or $CO_2$, which is necessarily the case when the catalyst is prepared by carrying out a reducing treatment ex situ, that is to say outside the reactor used for the hydrogenation of aromatic or polyaromatic compounds. In fact, when the reducing treatment is carried out ex situ, it is necessary to carry out a passivation step in order to preserve the metallic phase of the catalyst in the presence of air (during operations of transport and charging of the catalyst to the hydrogenation reactor), then to carry out a new step of reducing the catalyst.

The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one essential aspect of the preparation process according to the invention, said reducing treatment is carried out at a temperature above or equal to 150° C. and below 250° C., preferably between 160° C. and 230° C., and more preferentially between 170° C. and 220° C. The duration of the reducing treatment is between 5 minutes and less than 5 hours, preferably between 10 minutes and 4 hours, and even more preferentially between 10 minutes and 110 minutes.

The presence of the nickel-copper alloy at least partially in reduced form makes it possible to use operating conditions for reducing the nickel active phase which are less severe than in the prior art and thus makes it possible to carry out the reduction step directly within the reactor in which it is desired to carry out the hydrogenation of aromatic unsaturated compounds.

Furthermore, the presence of copper in the catalyst makes it possible to preserve good activity of the catalyst and a good service life of the catalyst when the latter is placed in contact with a hydrocarbon feedstock comprising sulfur. Indeed, compared to nickel, the copper present in the catalyst more easily captures the sulfur-containing compounds included in the feedstock, which limits the irreversible poisoning of the active sites. The rise in temperature up to the desired reduction temperature is generally slow, for example set between 0.1 and 10° C./min, preferably between 0.3 and 7° C./min.

The hydrogen flow rate, expressed in l/hour/gram of catalyst precursor, is between 0.01 and 100 l/hour/gram of catalyst, preferably between 0.05 and 10 l/hour/gram of catalyst precursor and more preferably still between 0.1 and 5 l/hour/gram of catalyst precursor.

Step h) Passivation (Optional)

The catalyst prepared according to the process according to the invention can advantageously undergo a passivation step with a sulfur-containing compound which makes it possible to improve the selectivity of the catalysts and to avoid thermal runaway during the start-up of new catalysts. The passivation generally consists in irreversibly poisoning, by the sulfur-containing compound, the most virulent active sites of the nickel which exist on the new catalyst and thus in weakening the activity of the catalyst in favor of its selectivity. The passivation step is carried out using methods known to those skilled in the art.

The passivation step with a sulfur-containing compound is generally carried out at a temperature of between 20° C. and 350° C., preferably between 40° C. and 200° C., for 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element relative to the total weight of the catalyst.

In one embodiment according to the invention, the preparation of the catalyst is carried out ex situ, that is to say before loading the catalyst into the reaction unit of the process for selective hydrogenation or hydrogenation of aromatics.

Selective Hydrogenation Process

Another subject of the present invention is a process for the selective hydrogenation of polyunsaturated compounds containing at least 2 carbon atoms per molecule, such as diolefins and/or acetylenics and/or alkenylaromatics, also known as styrenics, contained in a hydrocarbon feedstock having a final boiling point below or equal to 300° C., which process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst obtained by the preparation process as described above in the description.

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ fraction (hydrocarbon-based compounds having at least 5 carbon atoms), in particular diolefinic or styrene or indene compounds. These polyunsaturated compounds are highly reactive and result in side reactions in the polymerization units. It is thus necessary to remove them before making economic use of these fractions.

Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes. In the case of steam cracking gasolines used as feedstock, the selective hydrogenation also makes it possible to selectively hydrogenate the alkenylaromatics to give aromatics while avoiding the hydrogenation of the aromatic rings.

The hydrocarbon feedstock treated in the selective hydrogenation process has a final boiling point of below or equal to 300° C. and contains at least 2 carbon atoms per molecule and comprises at least one polyunsaturated compound. The term "polyunsaturated compounds" is intended to mean compounds comprising at least one acetylenic function and/or at least one diene function and/or at least one alkenylaromatic function.

More particularly, the feedstock is selected from the group consisting of a steam cracking C2 fraction, a steam cracking C2-C3 fraction, a steam cracking C3 fraction, a steam cracking C4 fraction, a steam cracking C5 fraction and a steam cracking gasoline, also known as pyrolysis gasoline or C5+ fraction.

The steam cracking C2 fraction, advantageously used for the implementation of the selective hydrogenation process according to the invention, exhibits, for example, the following composition: between 40% and 95% by weight of ethylene and of the order of 0.1% to 5% by weight of acetylene, the remainder being essentially ethane and methane. In some steam cracking C2 fractions, between 0.1% and 1% by weight of C3 compounds may also be present.

The steam cracking C3 fraction, advantageously used for the implementation of the selective hydrogenation process according to the invention, exhibits, for example, the following mean composition: of the order of 90% by weight of propylene and of the order of 1% to 8% by weight of propadiene and of methylacetylene, the remainder being essentially propane. In some C3 fractions, between 0.1% and 2% by weight of C2 compounds and of C4 compounds may also be present.

A C2-C3 fraction can also advantageously be used for the implementation of the selective hydrogenation process according to the invention. It exhibits, for example, the following composition: of the order of 0.1% to 5% by weight of acetylene, of the order of 0.1% to 3% by weight of propadiene and of methylacetylene, of the order of 30% by weight of ethylene and of the order of 5% by weight of propylene, the remainder being essentially methane, ethane and propane. This feedstock may also contain between 0.1% and 2% by weight of C4 compounds.

The steam cracking C4 fraction, advantageously used for the implementation of the selective hydrogenation process according to the invention, exhibits, for example, the following mean composition by weight: 1% by weight of butane, 46.5% by weight of butene, 51% by weight of butadiene, 1.3% by weight of vinylacetylene and 0.2% by weight of butyne. In some C4 fractions, between 0.1% and 2% by weight of C3 compounds and of C5 compounds may also be present.

The steam cracking C5 fraction, advantageously used for the implementation of the selective hydrogenation process according to the invention, exhibits, for example, the following composition: 21% by weight of pentanes, 45% by weight of pentenes and 34% by weight of pentadienes.

The steam cracking gasoline or pyrolysis gasoline, advantageously used for the implementation of the selective hydrogenation process according to the invention, corresponds to a hydrocarbon fraction, the boiling point of which is generally between 0 and 300° C., preferably between 10 and 250° C. The polyunsaturated hydrocarbons to be hydrogenated present in said steam cracking gasoline are in particular diolefin compounds (butadiene, isoprene, cyclopentadiene, and the like), styrene compounds (styrene, α-methylstyrene, and the like) and indene compounds (indene, and the like). The steam cracking gasoline generally comprises the C5-C12 fraction with traces of C3, C4, C13, C14 and C15 (for example between 0.1% and 3% by weight for each of these fractions). For example, a feedstock formed of pyrolysis gasoline generally has a composition as follows: 5% to 30% by weight of saturated compounds (paraffins and naphthenes), 40% to 80% by weight of aromatic compounds, 5% to 20% by weight of mono-olefins, 5% to 40% by weight of diolefins and 1% to 20% by weight of alkenylaromatic compounds, the combined compounds forming 100%. It also contains from 0 to 1000 ppm by weight of sulfur, preferably from 0 to 500 ppm by weight of sulfur.

Preferably, the polyunsaturated hydrocarbon feedstock treated in accordance with the selective hydrogenation process according to the invention is a steam cracking C2 fraction or a steam cracking C2-C3 fraction or a steam cracking gasoline.

The selective hydrogenation process according to the invention is targeted at removing said polyunsaturated hydrocarbons present in said feedstock to be hydrogenated without hydrogenating the monounsaturated hydrocarbons. For example, when said feedstock is a C2 fraction, the selective hydrogenation process is targeted at selectively hydrogenating acetylene. When said feedstock is a C3 fraction, the selective hydrogenation process is targeted at selectively hydrogenating propadiene and methylacetylene. In the case of a C4 fraction, the aim is to remove butadiene, vinylacetylene (VAC) and butyne; in the case of a C5 fraction, the aim is to remove the pentadienes. When said feedstock is a steam cracking gasoline, the selective hydrogenation process is targeted at selectively hydrogenating said polyunsaturated hydrocarbons present in said feedstock to be treated so that the diolefin compounds are partially hydrogenated to give mono-olefins and so that the styrene and indene compounds are partially hydrogenated to give corresponding aromatic compounds while avoiding the hydrogenation of the aromatic rings.

The technological implementation of the selective hydrogenation process is, for example, carried out by injection, as upflow or downflow, of the polyunsaturated hydrocarbon feedstock and of the hydrogen into at least one fixed bed reactor. Said reactor may be of isothermal type or of adiabatic type. An adiabatic reactor is preferred. The polyunsaturated hydrocarbon feedstock can advantageously be diluted by one or more reinjection(s) of the effluent, resulting from said reactor where the selective hydrogenation reaction takes place, at various points of the reactor, located between the inlet and the outlet of the reactor, in order to limit the temperature gradient in the reactor. The technological implementation of the selective hydrogenation process according to the invention can also advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The selective hydrogenation of the steam cracking C2, C2-C3, C3, C4, C5 and C5+ fractions can be carried out in the gas phase or in the liquid phase, preferably in the liquid phase for the C3, C4, C5 and C5+ fractions and in the gas phase for the C2 and C2-C3 fractions. A liquid-phase reaction makes it possible to lower the energy cost and to increase the cycle period of the catalyst.

Generally, the selective hydrogenation of a hydrocarbon feedstock containing polyunsaturated compounds containing at least 2 carbon atoms per molecule and having a final boiling point below or equal to 300° C. is carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity HSV (defined as the ratio of the flow rate by volume of feedstock to the volume of the catalyst) of between 0.1 and 200 $h^{-1}$ for a process carried out in the liquid phase, or at a hydrogen/(polyunsaturated compounds to be hydrogenated) mole ratio of between 0.5 and 1000 and at an hourly space velocity HSV of between 100 and 40 000 $h^{-1}$ for a process carried out in the gas phase.

In one embodiment according to the invention, when a selective hydrogenation process is carried out wherein the feedstock is a steam cracking gasoline comprising polyunsaturated compounds, the (hydrogen)/(polyunsaturated compounds to be hydrogenated) mole ratio is generally between 0.5 and 10, preferably between 0.7 and 5.0 and more preferably still between 1.0 and 2.0, the temperature is between 0° C. and 200° C., preferably between 20° C. and 200° C. and more preferably still between 30° C. and 180° C., the hourly space velocity (HSV) is generally between 0.5 and 100 $h^{-1}$, preferably between 1 and 50 $h^{-1}$, and the pressure is generally between 0.3 and 8.0 MPa, preferably between 1.0 and 7.0 MPa and more preferably still between 1.5 and 4.0 MPa.

More preferentially, a selective hydrogenation process is carried out wherein the feedstock is a steam cracking gasoline comprising polyunsaturated compounds, the hydrogen/(polyunsaturated compounds to be hydrogenated) mole ratio is between 0.7 and 5.0, the temperature is between 20° C. and 200° C., the hourly space velocity (HSV) is generally between 1 and 50 $h^{-1}$ and the pressure is between 1.0 and 7.0 MPa.

More preferentially still, a selective hydrogenation process is carried out wherein the feedstock is a steam cracking gasoline comprising polyunsaturated compounds, the hydrogen/(polyunsaturated compounds to be hydrogenated) mole ratio is between 1.0 and 2.0, the temperature is between 30° C. and 180° C., the hourly space velocity (HSV) is generally between 1 and 50 $h^{-1}$ and the pressure is between 1.5 and 4.0 MPa.

The hydrogen flow rate is adjusted in order to have available a sufficient amount thereof to theoretically hydrogenate all of the polyunsaturated compounds and to maintain an excess of hydrogen at the reactor outlet.

In another embodiment according to the invention, when a selective hydrogenation process is carried out wherein the feedstock is a steam cracking C2 fraction and/or a steam cracking C2-C3 fraction comprising polyunsaturated compounds, the (hydrogen)/(polyunsaturated compounds to be hydrogenated) mole ratio is generally between 0.5 and 1000, preferably between 0.7 and 800, the temperature is between 0° C. and 300° C., preferably between 15° C. and 280° C., the hourly space velocity (HSV) is generally between 100 and 40 000 $h^{-1}$, preferably between 500 and 30 000 $h^{-1}$, and the pressure is generally between 0.1 and 6.0 MPa, preferably between 0.2 and 5.0 MPa.

Aromatics Hydrogenation Process

Another subject of the present invention is a process for the hydrogenation of at least one aromatic or polyaromatic compound contained in a hydrocarbon feedstock having a final boiling point below or equal to 650° C., generally between 20° C. and 650° C., and preferably between 20° C. and 450° C. Said hydrocarbon feedstock containing at least one aromatic or polyaromatic compound can be chosen from the following petroleum or petrochemical fractions: the reformate from catalytic reforming, kerosene, light gas oil, heavy gas oil, cracking distillates, such as FCC recycle oil, coking unit gas oil or hydrocracking distillates.

The content of aromatic or polyaromatic compounds contained in the hydrocarbon feedstock treated in the hydrogenation process according to the invention is generally between 0.1 and 80% by weight, preferably between 1 to 50% by weight, and particularly preferably between 2 and 35% by weight, the percentage being based on the total weight of the hydrocarbon feedstock. The aromatic compounds present in said hydrocarbon feedstock are, for example, benzene or alkylaromatics, such as toluene, ethylbenzene, o-xylene, m-xylene or p-xylene, or also aromatics having several aromatic rings (polyaromatics), such as naphthalene.

The sulfur or chlorine content of the feedstock is generally less than 5000 ppm by weight of sulfur or chlorine, preferably less than 100 ppm by weight, and particularly preferably less than 10 ppm by weight.

The technological implementation of the process for the hydrogenation of aromatic or polyaromatic compounds is, for example, carried out by injection, as upflow or downflow, of the hydrocarbon feedstock and of the hydrogen into at least one fixed bed reactor. Said reactor may be of isothermal type or of adiabatic type. An adiabatic reactor is preferred. The hydrocarbon feedstock may advantageously be diluted by one or more reinjection(s) of the effluent, resulting from said reactor where the reaction for the hydrogenation of the aromatics takes place, at various points of the reactor, located between the inlet and the outlet of the reactor, in order to limit the temperature gradient in the reactor. The technological implementation of the process for the hydrogenation of the aromatics according to the invention may advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The hydrogenation of the aromatic or polyaromatic compounds may be carried out in the gas phase or in the liquid phase, preferably in the liquid phase. Generally, the hydrogenation of the aromatic or polyaromatic compounds is carried out at a temperature of between 30° C. and 350° C., preferably between 50° C. and 325° C., at a pressure of between 0.1 and 20 MPa, preferably between 0.5 and 10 MPa, at a hydrogen/(aromatic compounds to be hydrogenated) mole ratio between 0.1 and 10 and at an hourly space velocity HSV of between 0.05 and 50 $h^{-1}$, preferably between 0.1 and 10 $h^{-1}$, of a hydrocarbon feedstock containing aromatic or polyaromatic compounds and having a final boiling point below or equal to 650° C., generally between 20° C. and 650° C., and preferably between 20° C. and 450° C.

The hydrogen flow rate is adjusted in order to have available a sufficient amount thereof to theoretically hydrogenate all of the aromatic compounds and to maintain an excess of hydrogen at the reactor outlet.

The conversion of the aromatic or polyaromatic compounds is generally greater than 20 mol %, preferably greater than 40 mol %, more preferably greater than 80 mol %, and particularly preferably greater than 90 mol % of the aromatic or polyaromatic compounds contained in the hydrocarbon feedstock. The conversion is calculated by dividing the difference between the total moles of the aromatic or polyaromatic compounds in the hydrocarbon feedstock and in the product by the total moles of the aromatic or polyaromatic compounds in the hydrocarbon feedstock.

According to a specific alternative form of the process according to the invention, a process for the hydrogenation of the benzene of a hydrocarbon feedstock, such as the reformate resulting from a catalytic reforming unit, is carried out. The benzene content in said hydrocarbon feedstock is generally between 0.1 and 40% by weight, preferably between 0.5 and 35% by weight, and particularly preferably between 2 and 30% by weight, the percentage by weight being based on the total weight of the hydrocarbon feedstock.

The sulfur or chlorine content of the feedstock is generally less than 10 ppm by weight of sulfur or chlorine respectively, and preferably less than 2 ppm by weight.

The hydrogenation of the benzene contained in the hydrocarbon feedstock may be carried out in the gas phase or in the liquid phase, preferably in the liquid phase. When it is carried out in the liquid phase, a solvent may be present, such as cyclohexane, heptane or octane. Generally, the hydrogenation of the benzene is carried out at a temperature of between 30° C. and 250° C., preferably between 50° C. and 200° C., and more preferably between 80° C. and 180° C., at a pressure of between 0.1 and 10 MPa, preferably between 0.5 and 4 MPa, at a hydrogen/(benzene) mole ratio between 0.1 and 10 and at an hourly space velocity HSV of between 0.05 and 50 $h^{-1}$, preferably between 0.5 and 10 $h^{-1}$.

The conversion of the benzene is generally greater than 50 mol %, preferably greater than 80 mol %, more preferably greater than 90 mol % and particularly preferably greater than 98 mol %.

The invention will now be illustrated by the following examples which are in no way limiting.

EXAMPLES

Example 1: Preparation of the AL-1 Alumina

An alumina gel is synthesized via a mixture of sodium aluminate and aluminum sulfate. The precipitation reaction takes place at a temperature of 60° C., at a pH of 9, for 60 minutes and with stirring at 200 rpm.

The gel thus obtained is kneaded in a Z-arm mixer in order to provide the paste. The extrusion is carried out by passing the paste through a die provided with 1.6 mm-diameter orifices of trilobe shape. The extrudates thus obtained are dried under a stream of dry air at 150° C. for 12 hours and then calcined at 450° C. under a stream of dry air for 5 hours.

The extrudate undergoes a hydrothermal treatment at 650° C. in the presence of an aqueous solution containing acetic acid at 6.5% by weight relative to the weight of alumina for 3 hours in an autoclave, and then is calcined in dry air at 1000° C. for 2 hours in a tubular reactor. The AL-1 alumina is obtained.

The AL-1 alumina has a specific surface area of 80 $m^2/g$, a pore volume (determined by Hg porosimetry) of 0.85 ml/g and a mesopore diameter of 35 nm.

The sodium content is 0.0350% by weight relative to the total weight of the alumina and the sulfur content is 0.15% by weight relative to the total weight of the alumina.

Example 1a: Preparation of the AL-2 Alumina

An alumina gel is synthesized via a mixture of sodium aluminate and aluminum sulfate. The precipitation reaction takes place at a temperature of 60° C., at a pH of 9, for 60 minutes and with stirring at 200 rpm.

The gel thus obtained is kneaded in a Z-arm mixer in order to provide the paste. The extrusion is carried out by passing the paste through a die provided with 1.6 mm-diameter orifices of trilobe shape. The extrudates thus obtained are dried under a stream of dry air at 150° C. for 12 hours and then calcined at 450° C. under a stream of dry air for 5 hours. The AL-2 alumina is obtained.

The AL-2 alumina has a specific surface area of 255 $m^2/g$, a pore volume (determined by Hg porosimetry) of 0.7 ml/g and a mesopore diameter of 12 nm.

The sodium content is 0.0350% by weight relative to the total weight of the alumina and the sulfur content is 0.15% by weight relative to the total weight of the alumina.

Example 2: Preparation of an Aqueous Solution of Ni Precursors

The aqueous solution of Ni precursors (solution S1) used for the preparation of the catalyst A is prepared by dissolving 43.5 g of nickel nitrate ($NiNO_3$, supplier Strem Chemicals®) in a volume of 13 ml of distilled water. The solution S1, the Ni concentration of which is 350 g of Ni per liter of solution, is obtained.

Example 3: Preparation of an Aqueous Solution of Ni Precursors with Organic Compound The aqueous solution of Ni precursors (solution S2) used for the preparation of the catalysts B to G is prepared by dissolving 43.5 g of nickel nitrate ($NiNO_3$, supplier Strem Chemicals®) and malonic acid (CAS 141-82-2; supplier Fluka®) in a volume of 13 ml of distilled water. The additive/Ni mole ratio being 0.5. The solution S2, the Ni concentration of which is 350 g of Ni per liter of solution, is obtained.

Example 4: Preparation of an Aqueous Solution of the Precursors of the NiCu Alloy (5% Ni)

The aqueous solution of Ni precursors (solution S3) used for the preparation of the catalysts C, D, E, and G is prepared by dissolving 14.5 g of nickel nitrate ($NiNO_3$, supplier Strem Chemicals®) in a volume of 13 ml of distilled water. A solution, the Ni concentration of which is 116.6 g of Ni per liter of solution, is obtained. The copper nitrate precursor is then added in order to have in particular an Ni/Cu mole ratio of 3 (catalysts C to F). The solution S3 is obtained. It makes it possible to introduce the precursors of the NiCu alloy with a weight content of Ni relative to the final catalyst of about 5 wt %.

Example 5: Preparation of a Catalyst A

The solution S2 prepared in example 3 is dry impregnated, by adding it dropwise, on 10 g of AL-1 alumina obtained according to example 1.

The solid thus obtained is subsequently dried in an oven at 120° C. for 12 hours and then calcined under a stream of dry air of 1 l/h/g of catalyst at 450° C. for 2 hours.

The dry air used in this example and in all the examples below contains less than 5 grams of water per kilogram of air.

The catalyst precursor thus obtained is dry impregnated with an aqueous solution containing formic acid with the HCOOH/Ni mole ratio equal to 1 mol/mol.

At the end of the impregnation of the aqueous solution containing formic acid, the catalyst precursor undergoes a heat treatment at 150° C., for 2 hours under a stream of air containing 50 grams of water per kilogram of dry air with a flow rate of 1 l/h/g of catalyst, then for 1 hour at 120° C. under a stream of dry air.

Then the solution S3 is dry impregnated on the above catalyst precursor. The Ni content targeted in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 12 below. Catalyst A is obtained, the characteristics of which are reported in tables 1 and 2 below.

Example 6: Preparation of a Catalyst B According to the Invention

The solution S3 is dry impregnated dropwise on 10 g of the AL-1 support. The Ni content targeted in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours. The precursor of the final catalyst, B', is obtained.

Next, the solution S2 prepared in example 3 is dry impregnated, by adding it dropwise, the final catalyst precursor B'.

The solid thus obtained is subsequently dried in an oven at 120° C. for 12 hours and then calcined under a stream of dry air of 1 l/h/g of catalyst at 450° C. for 2 hours.

The catalyst precursor obtained is dry impregnated with an aqueous solution containing formic acid with the HCOOH/Ni mole ratio equal to 1 mol/mol.

At the end of the impregnation of the aqueous solution containing formic acid, the catalyst precursor undergoes a heat treatment at 150° C., for 2 hours under a stream of air containing 50 grams of water per kilogram of dry air with a flow rate of 1 l/h/g of catalyst, then for 1 hour at 120° C. under a stream of dry air. The catalyst precursor is then reduced under the conditions as described in example 12 below.

Catalyst B is obtained, the characteristics of which are reported in tables 1 and 2 below.

Example 7: Preparation of a Catalyst C (Not in Accordance with the Invention)

The S3 solution is dry impregnated dropwise on 10 g of the AL-1 support. The Ni content targeted in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours.

The precursor of the final catalyst, C', is obtained.

The solution S1 prepared in example 2 is then dry impregnated, by adding it dropwise, the catalyst precursor C'.

The solid thus obtained is subsequently dried in an oven at 120° C. for 12 hours and then calcined under a stream of dry air of 1 l/h/g of catalyst at 450° C. for 2 hours.

The catalyst precursor thus obtained is dry impregnated with an aqueous solution containing formic acid with the HCOOH/Ni mole ratio equal to 1 mol/mol.

At the end of the impregnation of the aqueous solution containing formic acid, the catalyst precursor undergoes a heat treatment at 150° C., for 2 hours under a stream of air containing 50 grams of water per kilogram of dry air with a flow rate of 1 l/h/g of catalyst, then for 1 hour at 120° C. under a stream of dry air. The catalyst precursor is then reduced under the conditions as described in example 12 below.

Catalyst C is obtained, the characteristics of which are reported in tables 1 and 2 below.

Example 8: Preparation of a Catalyst D (Not in Accordance with the Invention)

The S3 solution is dry impregnated dropwise on 10 g of the AL-2 support. The Ni content targeted in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours.

The precursor of the final catalyst, D', is obtained.

The solution S2 prepared in example 3 is then dry impregnated, by adding it dropwise, on the final catalyst precursor D'.

The solid thus obtained is subsequently dried in an oven at 120° C. for 12 hours and then calcined under a stream of dry air of 1 l/h/g of catalyst at 450° C. for 2 hours.

The catalyst precursor thus obtained is dry impregnated with an aqueous solution containing formic acid with the HCOOH/Ni mole ratio equal to 1 mol/mol.

At the end of the impregnation of the aqueous solution containing formic acid, the catalyst precursor undergoes a heat treatment at 150° C., for 2 hours under a stream of air containing 50 grams of water per kilogram of dry air with a flow rate of 1 l/h/g of catalyst, then for 1 hour at 120° C. under a stream of dry air. The catalyst precursor is then reduced under the conditions as described in example 12 below.

Catalyst D is obtained, the characteristics of which are reported in tables 1 and 2 below.

Example 9: Preparation of a Catalyst E (Not in Accordance with the Invention)

The solution S2 prepared in example 3 is dry impregnated, by adding it dropwise, on 10 g of AL-1 alumina obtained according to example 1.

The solid thus obtained is subsequently dried in an oven at 120° C. for 12 hours and then calcined under a stream of dry air of 1 l/h/g of catalyst at 450° C. for 2 hours.

The dry air used in this example and in all the examples below contains less than 5 grams of water per kilogram of air.

The catalyst precursor E' thus obtained is dry impregnated with an aqueous solution containing formic acid with the HCOOH/Ni mole ratio equal to 1 mol/mol.

At the end of the impregnation of the aqueous solution containing formic acid, the catalyst precursor undergoes a heat treatment at 150° C., for 2 hours under a stream of air containing 50 grams of water per kilogram of dry air with a flow rate of 1 l/h/g of catalyst, then for 1 hour at 120° C. under a stream of dry air.

Catalyst E is obtained, the characteristics of which are reported in tables 1 and 2 below. The catalyst precursor is then reduced under the conditions as described in example 12 below.

Example 10: Preparation of a Catalyst F (not in Accordance with the Invention)

The S3 solution is dry impregnated dropwise on 10 g of the AL-1 support. The Ni content targeted in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours.

The precursor of the final catalyst, F', is obtained.

The solution S2 prepared in example 3 is then dry impregnated, by adding it dropwise, on the catalyst precursor F'.

The solid thus obtained is subsequently dried in an oven at 120° C. for 12 hours and then calcined under a stream of dry air of 1 l/h/g of catalyst at 450° C. for 2 hours.

Catalyst F is obtained, the characteristics of which are reported in tables 1 and 2 below. The catalyst precursor is then reduced under the conditions as described in example 12 below.

Example 11: Preparation of a Catalyst G (Not in Accordance with the Invention)

The solution S2 prepared in example 3 is dry impregnated, by adding it dropwise, on 10 g of AL-1 alumina obtained according to example 1.

The solid thus obtained is subsequently dried in an oven at 120° C. for 12 hours and then calcined under a stream of dry air of 1 l/h/g of catalyst at 450° C. for 2 hours. The catalyst precursor is then reduced under the conditions as described in example 9 below.

Catalyst G is obtained, the characteristics of which are reported in tables 1 and 2 below. The catalyst precursor is then reduced under the conditions as described in example 12 below.

Example 12: Characterization

All the catalysts contain the contents targeted during impregnation, that is to say 15% of nickel element (characterized by X-ray fluorescence) relative to the total weight of the catalyst, and the % of copper added (characterized by X-ray fluorescence).

The amount of alloy obtained after the calcining then reduction step was determined by X-ray diffraction (XRD) analysis on samples of catalyst in powder form.

The amount of nickel in metallic form obtained after the reduction step was determined by X-ray diffraction (XRD) analysis on samples of catalyst in powder form. Between the reduction step and throughout the duration of the characterization by XRD, the catalysts are never returned to the open air. The diffraction patterns are obtained by radiocrystallographic analysis by means of a diffractometer using the conventional powder method with $K\alpha 1$ radiation of copper ($\lambda=1.5406$ Å).

The degree of reduction was calculated by calculating the area of the line of $Ni^0$ located around 52°2θ, on all of the diffractograms of each sample of catalyst analyzed, then by subtracting the signal present as soon as ambient temperature is reached under the line at 52°, which is due to alumina.

Table 1 below collates the degrees of reduction or else the content of nickel metal $Ni^0$ (expressed as % by weight relative to the total weight of "active" nickel, i.e. without taking into account the nickel that makes up the alloy) for all the catalysts A to G characterized by XRD after a reduction step at 170° C. for 90 minutes under a hydrogen stream. These values were also compared with the degree of reduction obtained for catalyst G (Ni alone) after a conventional reduction step (that is to say at a temperature of 400° C. for 15 hours under a hydrogen stream).

Alumina in delta and theta form and large CuO and NiO lines are detected at ambient temperature on all the copper- and nickel-containing catalysts, after calcination.

A line corresponding to the alloy in $Ni_{0.76}Cu_{0.24}$ form is moreover detected after reduction.

In order to evaluate the degree of reducibility and therefore the formation of $Ni^0$, the area of the line of $Ni^0$ located around 52°2θ is measured, on all the diffractograms, by subtracting the signal present as soon as ambient temperature is reached under the line at 52°, which is due to the alumina. It is thus possible to determine the relative percentage of $Ni^0$ crystallized after reduction.

Table 1 below summarizes the degrees of reducibility or the $Ni^0$ content for all the catalysts characterized by XRD after reduction at 170° C. for 90 minutes under a hydrogen stream. These values were also compared with the degree of reduction obtained for catalyst G (Ni alone) after a conventional reduction step (that is to say at a temperature of 400° C. for 15 hours under a hydrogen stream).

TABLE 1

| Catalyst | Final reduction | Ni content for the 1st imp. (wt %) | Ni content for 2nd imp. (wt %) | Ni/Cu mole ratio | Percentage of Ni° alone (XRD) after reduction (%) |
|---|---|---|---|---|---|
| A (invention) | 170° C., 90 min | 15 | 5 | 3 | 90 |
| B (invention) | 170° C., 90 min | 5 | 15 | 3 | 95 |
| C (comparative) | 170° C., 90 min | 5 | 15 | 3 | 100 |
| D (comparative) | 170° C., 90 min | 5 | 15 | 3 | 100 |
| E (comparative) | 170° C., 90 min | — | 15 | — | 0 |
| F (comparative) | 170° C., 90 min | 5 | 15 | — | 95 |
| G (comparative) | 170° C., 90 min | 15 | — | — | 70 |
| G (comparative) | 400° C., 15 h | 15 | — | — | 0 |

TABLE 2

| Catalyst | Support | Addition NiCu | Particle size (nm)* | Crust thickness/ grain diameter (%) | Ni density ratio between crust and core ($d_{crust}/d_{core}$) | Ni content in crust/total Ni (%) |
|---|---|---|---|---|---|---|
| A | AL-1 | Post-impregnation | 2.2 | 6.8 | 5 | 66 |
| B | AL-1 | Pre-impregnation | 2.1 | 5 | 11 | 72 |
| C (not in accordance) | AL-1 | Pre-impregnation | 14 | 4.2 | 6 | 65 |
| D (not in accordance) | AL-2 | Pre-impregnation | 10.2 | Homogeneous distribution | — | — |
| E (not in accordance) | AL-1 | — | 3 | 7 | 8 | 68 |
| F (not in accordance) | AL-1 | Pre-impregnation | 2.5 | Homogeneous distribution | — | — |
| G (not in accordance) | AL-1 | — | 2.4 | Homogeneous distribution | — | — |

*Particle size of the 15% of nickel which does not make up the alloy.

Example 13: Catalytic Tests: Performance in Selective Hydrogenation of a Mixture Containing Styrene and Isoprene ($A_{HYD1}$)

Catalysts A to G described in the above examples are tested with regard to the reaction for the selective hydrogenation of a mixture containing styrene and isoprene.

The composition of the feedstock to be selectively hydrogenated is as follows: 8% by weight of styrene (supplied by Sigma Aldrich®, purity 99%), 8% by weight of isoprene (supplied by Sigma Aldrich®, purity 99%) and 84% by weight of n-heptane (solvent) (supplied by VWR®, purity >99% Chromanorm HPLC). This composition corresponds to the initial composition of the reaction mixture. This mixture of model molecules is representative of a pyrolysis gasoline. The selective hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

214 ml of n-heptane (supplied by VWR®, purity >99% Chromanorm HPLC) and an amount of 3 ml of catalyst are added to an autoclave. The autoclave is closed and purged. The autoclave is then pressurized under 35 bar (3.5 MPa) of hydrogen. The catalyst is first reduced in situ, at 170° C. for 90 minutes under a hydrogen stream of 1 l/h/g (temperature rise gradient of 1° C./min) for catalysts A to G (which corresponds here to step g) of the preparation process according to the invention according to one embodiment).

The autoclave is then brought to the test temperature, equal to 30° C. At time t=0, approximately 30 g of a mixture containing styrene, isoprene and n-heptane are introduced into the autoclave. The reaction mixture then has the composition described above and stirring is started at 1600 rpm. The pressure is kept constant at 35 bar (3.5 MPa) in the autoclave using a storage cylinder located upstream of the reactor. Another test was carried out for catalyst A, but with a catalyst reduction temperature of 400° C. for 15 hours.

The progress of the reaction is monitored by taking samples from the reaction medium at regular time intervals: the styrene is hydrogenated to give ethylbenzene, without hydrogenation of the aromatic ring, and the isoprene is hydrogenated to give methylbutenes. If the reaction is prolonged for longer than necessary, the methylbutenes are in their turn hydrogenated to give isopentane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to G are reported in table 3 below. They are related to the catalytic activity ($A_{HYD1}$) measured for catalyst A prepared under conventional reduction conditions (at a temperature of 400° C. for 16 hours under a hydrogen stream).

Example 14: Catalytic Tests: Performance in Hydrogenation of Toluene ($A_{HYD2}$)

Catalysts A to G described in the above examples are also tested with regard to the reaction for the hydrogenation of toluene. The selective hydrogenation reaction is carried out in the same autoclave as that described in Example 13.

214 ml of n-heptane (supplied by VWR®, purity >99% Chromanorm HPLC) and an amount of 3 ml of catalyst are added to an autoclave. The autoclave is closed and purged. The autoclave is then pressurized under 35 bar (3.5 MPa) of hydrogen. The catalyst is first reduced in situ, at 170° C. for 90 minutes under a hydrogen stream of 1 l/h/g (temperature rise gradient of 1° C./min) for catalysts A to G (which corresponds here to step g) of the preparation process according to the invention according to one embodiment). After addition of 216 ml of n-heptane (supplied by VWR®, purity >99% Chromanorm HPLC), the autoclave is closed, purged, then pressurized under 35 bar (3.5 MPa) of hydrogen and brought to the test temperature, equal to 80° C. At time t=0, approximately 26 g of toluene (supplied by SDS®, purity >99.8%) are introduced into the autoclave (the initial composition of the reaction mixture is then 6 wt % toluene/

94 wt % n-heptane) and stirring is started at 1600 rpm. The pressure is kept constant at 35 bar (3.5 MPa) in the autoclave using a storage cylinder located upstream of the reactor. The progress of the reaction is monitored by taking samples from the reaction medium at regular time intervals: the toluene is completely hydrogenated to give methylcyclohexane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to G are reported in table 3 below. They are related back to the catalytic activity ($A_{HYD2}$) measured for catalyst C. For comparison, catalyst G was also prepared under conventional reduction conditions (at a temperature of 400° C. for 16 hours under a hydrogen stream in an ex situ flow-through reactor).

TABLE 3

| Catalyst | Reduction (°C.) | $A_{HYD1}$ (%) | $A_{HYD2}$ (%) |
|---|---|---|---|
| A (in accordance) | 170° C., 16 h | 180 | 175 |
| B (in accordance) | 170° C., 16 h | 175 | 170 |
| C (not in accordance) | 170° C., 16 h | 100 | 100 |
| D (not in accordance) | 170° C., 16 h | 60 | 70 |
| E (not in accordance) | 170° C., 16 h | <1 | <1 |
| F (not in accordance) | 170° C., 16 h | 55 | 45 |
| G (not in accordance) | 170° C., 16 h | <1 | <1 |
| G (not in accordance) | 400° C., 16 h | 120 | 135 |

Comparison of the performance in the selective hydrogenation of a mixture containing styrene and isoprene ($A_{HYD1}$) and in the hydrogenation of toluene ($A_{HYD2}$)

This clearly shows the improved $A_{HYD1}$ and $A_{HYD2}$ performance of the catalysts A, B according to the invention, compared to catalysts C to G not in accordance with the invention. Catalysts A and B are reduced at 170° C. to a level of at least 90% and have particles of small size, which are distributed in an "eggshell". Catalyst C has large particles due to the use of solution S2 without additives. Its catalytic activity remains advantageous owing to the presence of 100% of reduced Ni due to the addition of NiCu. Catalysts D and F indeed have small particles that are reduced to a level of 90%, but they are not distributed in a crust, hence the activity in decline. Catalysts E and G, despite small particles, are not active. The absence of NiCu does not make it possible to obtain reduced Ni, the active phase in hydrogenation, at 170° C.

The invention claimed is:

1. A catalyst comprising nickel and copper, in a proportion of 1% and 50% by weight of nickel element relative to the total weight of the catalyst, and a second metallic element of copper, in a proportion of 0.5% to 15% by weight of copper element relative to the total weight of the catalyst, and an alumina support, wherein in said catalyst:
    the nickel is distributed both on a crust at the periphery of the support, and in the core of the support, the thickness of said crust being between 2% and 15% of the diameter of the catalyst;
    the nickel density ratio between the crust and the core is strictly greater than 3;
    said crust comprises more than 25% by weight of nickel element relative to the total weight of nickel contained in the catalyst;
    the mole ratio between nickel and copper is between 0.5 and 5;
    at least one portion of the nickel and copper is in the form of a nickel-copper alloy;
    the nickel content in the nickel-copper alloy is between 0.5% and 15% by weight of nickel element relative to the total weight of the catalyst,
    the nickel being in the form of particles in oxide form and having a size of less than 7 nm.

2. The catalyst as claimed in claim 1, wherein the nickel density ratio between the crust and the core is greater than or equal to 3.5.

3. The catalyst as claimed in claim 1, wherein said crust comprises more than 40% by weight of nickel element relative to the total weight of nickel contained in the catalyst.

4. The catalyst as claimed in claim 1, wherein the transition interval between the core and the crust of the catalyst is between 0.05% and 3% of the diameter of the catalyst.

5. The catalyst as claimed in claim 1, wherein the size of the nickel particles in oxide form is less than 5 nm.

6. The catalyst as claimed in claim 1, wherein the sulfur content of the alumina support is between 0.001% and 2% by weight relative to the total weight of the alumina support, and the sodium content of said alumina support is between 0.001% and 2% by weight relative to the total weight of said alumina gel.

7. The catalyst as claimed in claim 1, wherein the thickness of said crust is between 2.5% and 12% of the diameter of the catalyst.

8. The catalyst as claimed in claim 1, wherein the nickel density ratio between the crust and the core is between 3.8 and 15.

9. A process for preparing the catalyst as claimed in claim 1, comprising
    a) providing an alumina gel;
    b) shaping the alumina gel from step a);
    c) subjecting the shaped alumina gel obtained at the end of step b) to a heat treatment comprising at least one hydrothermal treatment step in an autoclave in the presence of an acid solution, at a temperature of between 100° C. and 800° C., and at least one calcining step, at a temperature of between 400° C. and 1500° C., carried out after the hydrothermal treatment step, in order to obtain an alumina support;
    d) carrying out a sequence of the following sub-steps:
        d1) bringing the alumina support into contact with at least one nickel precursor in order to obtain a catalyst precursor,
        d2) drying the catalyst precursor obtained at the end of step d1) at a temperature below 250° C.;
        d3) bringing the dried catalyst precursor obtained at the end of step d2) into contact with at least one solution containing at least one organic additive chosen from aldehydes containing 1 to 14 carbon atoms per molecule, ketones or polyketones containing 3 to 18 carbon atoms per molecule, ethers or esters containing 2 to 14 carbon atoms per molecule, alcohols or polyalcohols containing 1 to 14 carbon atoms per molecule or carboxylic acids or polycarboxylic acids containing 1 to 14 carbon atoms per molecule, the mole ratio between the organic additive and the nickel being greater than 0.05 mol/mol;
        d4) carrying out a hydrothermal treatment of the catalyst precursor obtained at the end of step d3) at a temperature between 100° C. and 200° C. for a period of between 30 minutes and 5 hours under a gas stream comprising between 5 and 650 grams of water per kg of dry gas;
    e) carrying out a sequence of the following sub-steps:
        e1) bringing the alumina support into contact with at least one solution containing at least one copper precursor and one nickel precursor at a predetermined nickel concentration in order to obtain, on the final catalyst, a content of between 0.5% and 15% by weight of nickel element relative to the total weight of the final catalyst;

e2) drying, in at least one step, the catalyst precursor obtained at the end of step e1) at a temperature below 250° C.;

steps d) and e) being carried out separately in any order, f) bringing the alumina support into contact with at least one solution containing at least one organic compound comprising at least one carboxylic acid function, or at least one alcohol function, or at least one ester function, or at least one amide function, or at least one amine function, step f) being carried out, either at the same time as sub-step d1) of step d), or before or after step d), but before step g), it being understood that when step f) is carried out before or after step d), then said step f) includes drying of the catalyst precursor at a temperature below 250° C. after bringing the support into contact with said solution comprising at least one organic compound;

g) reducing the catalyst precursor resulting from steps a) to f) by bringing said catalyst precursor into contact with a reducing gas at a temperature above or equal to 150° C. and below 250° C.

10. The process as claimed in claim 9, wherein the mole ratio between said organic compound introduced in step f) and the nickel element also introduced in step d1) is between 0.01 and 5.0 mol/mol.

11. The process as claimed in claim 9, wherein steps d1) and f) are carried out at the same time.

12. The process as claimed in claim 9, wherein the organic compound of step f) is chosen from oxalic acid, malonic acid, glycolic acid, lactic acid, tartronic acid, citric acid, tartaric acid, pyruvic acid, levulinic acid, ethylene glycol, propane-1,3-diol, butane-1,4-diol, glycerol, xylitol, mannitol, sorbitol, diethylene glycol, glucose, gamma-valerolactone, dimethyl carbonate, diethyl carbonate, formamide, N-methylformamide, acetamide, N-methylacetamide, N,N-dimethylmethanamide, 2-pyrrolidone, γ-lactam, lactamide, urea, alanine, arginine, lysine, proline, serine, and EDTA.

13. The process as claimed in claim 9, wherein the copper precursor is chosen from copper acetate, copper acetylacetonate, copper nitrate, copper sulfate, copper chloride, copper bromide, copper iodide and copper fluoride.

14. The process as claimed in claim 9, in which, in step d3), the organic additive is chosen from formic acid, formaldehyde, acetic acid, citric acid, oxalic acid, glycolic acid, malonic acid, ethanol, methanol, ethyl formate, methyl formate, paraldehyde, acetaldehyde, gamma-valerolactone, glucose, sorbitol and trioxane.

15. The process as claimed in claim 9, wherein the mole ratio between the organic additive introduced in step d2) and the nickel is between 0.1 and 5 mol/mol.

16. The process as claimed in claim 9, wherein the organic compound of step f) is different from the organic additive of step d2).

17. A process for the selective hydrogenation of polyunsaturated compounds containing at least 2 carbon atoms per molecule, contained in a hydrocarbon feedstock having a final boiling point below or equal to 300° C., which process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst as claimed in claim 1.

18. A process for the hydrogenation of at least one aromatic or polyaromatic compound contained in a hydrocarbon feedstock having a final boiling point below or equal to 650° C., said process being carried out in the gas phase or in the liquid phase, at a temperature of between 30° C. and 350° C., at a pressure of between 0.1 and 20 MPa, at a hydrogen/(aromatic compounds to be hydrogenated) mole ratio of between 0.1 and 10 and at an hourly space velocity HSV of between 0.05 and 50 $h^{-1}$, in the presence of a catalyst as claimed in claim 1.

* * * * *